US011076981B2

(12) United States Patent
Swonger et al.

(10) Patent No.: US 11,076,981 B2
(45) Date of Patent: *Aug. 3, 2021

(54) HIGH PURITY LITHIUM AND ASSOCIATED PROCESSES

(71) Applicant: ALPHA-EN CORPORATION, Yonkers, NY (US)

(72) Inventors: Lawrence Ralph Swonger, Lititz, PA (US); Emilie Bodoin, Bedford Hills, NY (US)

(73) Assignee: alpha-En Corporation, Yonkers, NY (US)

( * ) Notice: Subject to any disclaimer, the term of this patent is extended or adjusted under 35 U.S.C. 154(b) by 126 days.

This patent is subject to a terminal disclaimer.

(21) Appl. No.: 16/160,522

(22) Filed: Oct. 15, 2018

(65) Prior Publication Data

US 2019/0051885 A1 Feb. 14, 2019

Related U.S. Application Data

(62) Division of application No. 15/160,013, filed on May 20, 2016, now Pat. No. 10,177,366.

(60) Provisional application No. 62/168,770, filed on May 30, 2015, provisional application No. 62/183,300, filed on Jun. 23, 2015, provisional application No. 62/284,812, filed on Oct. 9, 2015.

(51) Int. Cl.
| | |
|---|---|
| *H01M 4/04* | (2006.01) |
| *H01M 4/38* | (2006.01) |
| *H01M 4/1395* | (2010.01) |
| *H01M 4/134* | (2010.01) |
| *H01M 10/0525* | (2010.01) |
| *C25C 1/02* | (2006.01) |
| *C25D 3/42* | (2006.01) |
| *A61F 5/56* | (2006.01) |
| *C25C 7/00* | (2006.01) |
| *A61N 1/378* | (2006.01) |
| *H04R 25/00* | (2006.01) |
| *A61N 1/362* | (2006.01) |
| *C25D 7/00* | (2006.01) |
| *C25D 17/00* | (2006.01) |
| *C25D 17/10* | (2006.01) |
| *H01M 10/052* | (2010.01) |
| *H01M 6/14* | (2006.01) |
| *A61N 1/39* | (2006.01) |
| *A61N 1/36* | (2006.01) |
| *B60L 50/64* | (2019.01) |

(52) U.S. Cl.
CPC ............ *A61F 5/566* (2013.01); *A61N 1/3629* (2017.08); *A61N 1/378* (2013.01); *C25C 1/02* (2013.01); *C25C 7/00* (2013.01); *C25D 3/42* (2013.01); *C25D 7/00* (2013.01); *C25D 17/002* (2013.01); *C25D 17/10* (2013.01); *H01M 4/0404* (2013.01); *H01M 4/0452* (2013.01); *H01M 4/134* (2013.01); *H01M 4/1395* (2013.01); *H01M 4/382* (2013.01); *H01M 10/0525* (2013.01); *H04R 25/606* (2013.01); *A61M 2205/8206* (2013.01); *A61N 1/36* (2013.01); *A61N 1/39* (2013.01); *B60L 50/64* (2019.02); *H01M 6/14* (2013.01); *H01M 10/052* (2013.01); *H01M 2220/20* (2013.01); *H01M 2220/30* (2013.01); *H04R 2225/31* (2013.01); *H04R 2225/67* (2013.01); *Y02E 60/10* (2013.01)

(58) Field of Classification Search
CPC .......... H01M 10/052; H01M 10/0525; H01M 2220/20; H01M 2220/30; H01M 4/0404; H01M 4/0452; H01M 4/134; H01M 4/1395; H01M 4/382; H01M 6/14; C25C 1/02; C25D 3/42

See application file for complete search history.

(56) References Cited

U.S. PATENT DOCUMENTS

| | | | |
|---|---|---|---|
| 4,973,390 A | 11/1990 | Christini et al. | |
| 4,988,417 A * | 1/1991 | DeYoung | C25C 3/02 204/243.1 |
| 5,219,550 A | 6/1993 | Brown et al. | |
| 5,318,600 A | 6/1994 | Schlaikjet et al. | |
| 5,458,997 A | 10/1995 | Crespi et al. | |

(Continued)

FOREIGN PATENT DOCUMENTS

| | | |
|---|---|---|
| CN | 1299884 | 6/2001 |
| CN | 103031568 | 4/2013 |

(Continued)

OTHER PUBLICATIONS

Y. Sato, O. Takeda. Hydrogen Storage and Transportation System through Lithium Hydride Using Molten Salt Technology, Molten Salts Chemistry, 2013, 451-470.*

Extended European Search Report issued in related European Patent Application No. 16803991.5 dated Mar. 13, 2019.

(Continued)

*Primary Examiner* — Carlos Barcena

(57) ABSTRACT

High purity lithium and associated products are provided. In a general embodiment, the present disclosure provides a lithium metal product in which the lithium metal is obtained using a selective lithium ion conducting layer. The selective lithium ion conducting layer includes an active metal ion conducting glass or glass ceramic that conducts only lithium ions. The present lithium metal products produced using a selective lithium ion conducting layer advantageously provide for improved lithium purity when compared to commercial lithium metal. Pursuant to the present disclosure, lithium metal having a purity of at least 99.96 weight percent on a metals basis can be obtained.

5 Claims, 17 Drawing Sheets

(56) References Cited

U.S. PATENT DOCUMENTS

| | | | |
|---|---|---|---|
| 6,071,489 A | 6/2000 | Sun et al. | |
| 2003/0157403 A1* | 8/2003 | Shelekhin | H01M 2/0277 |
| | | | 429/159 |
| 2004/0111874 A1 | 6/2004 | Brown et al. | |
| 2007/0160516 A1 | 7/2007 | Boryta et al. | |
| 2010/0323118 A1 | 12/2010 | Mohanty et al. | |
| 2011/0200508 A1* | 8/2011 | Harrison | C25B 1/26 |
| | | | 423/276 |
| 2011/0300444 A1 | 12/2011 | Nakamura | |
| 2011/0316484 A1 | 12/2011 | De Wit et al. | |
| 2012/0251891 A1 | 10/2012 | Li et al. | |
| 2014/0076734 A1 | 3/2014 | Calvo et al. | |
| 2014/0125292 A1 | 5/2014 | Best et al. | |
| 2014/0178774 A1 | 6/2014 | Kim et al. | |
| 2015/0014184 A1 | 1/2015 | Swonger | |

FOREIGN PATENT DOCUMENTS

| | | |
|---|---|---|
| CN | 103031598 | 4/2013 |
| CN | 103560237 | 2/2014 |
| CN | 102838102 | 11/2014 |
| WO | 2017131051 | 8/2017 |

OTHER PUBLICATIONS

International Search Report and Written Opinion issued in related International Patent Application No. PCT/US2016/033445 dated Oct. 5, 2016.
T. Hoshino, "Innovative Separation Technology for Lithium-6 Enrichment Using Electrodialysis with Lithium Ionic Superconductor," Quantum and Radiological Science and Technology, downloaded from Internet Oct. 2, 2017, https://ecs.confex.com/ecs/232/webprogram/Paper105309.html. 2 pages.
J. Black et al., "Electrochemical Isotope Effect and Lithium Isotope Separation," J. Am. Chem. Soc., 2009, 131 (29), pp. 9904-9905.
Chen et al., "Porous layered lithium-rich oxide nanorods: Synthesis and performances as cathode of lithium ion battery," Electrochimica Acta, vol. 154, 83-93 (2015).
Examination Report issued in Appl. No. EP 16803991.5 (dated 2020).
Song et al., "Mo-doped $LiV_3O_8$ nanorod-assembled nanosheets as a high performance cathode material for lithium ion batteries," J. Mater. Chem. A, 3(7): 3547-3558 (2015).
Communication issued in EP16803991.5 (dated Dec. 10, 2020).
Examination Report No. 1 issued in AU2016270313 (dated Oct. 31, 2020).
Office Action issued in JP2018-513724 (dated Oct. 20, 2020).

* cited by examiner

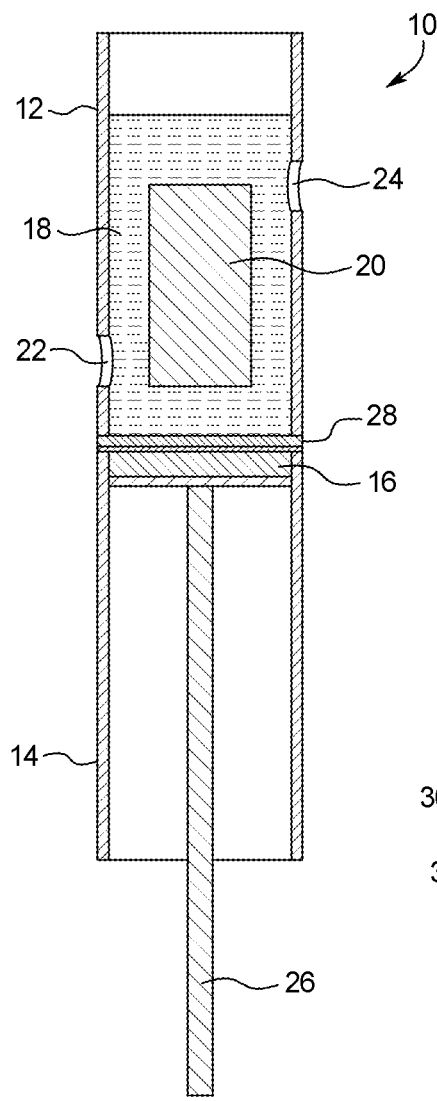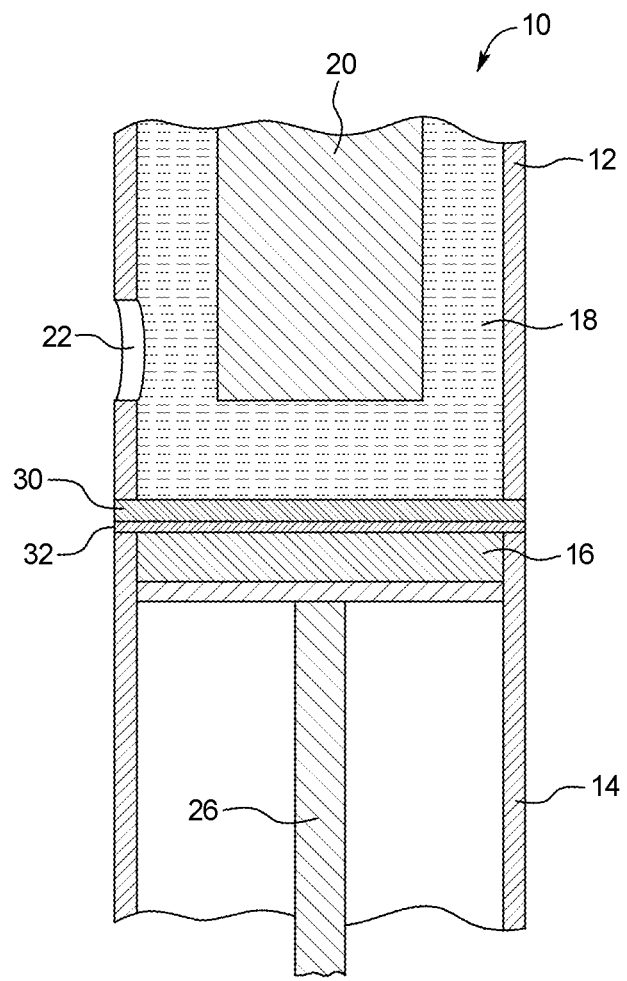
FIG. 1
FIG. 2

HIGH PURITY LITHIUM AND ASSOCIATED PROCESSES

PRIORITY CLAIM

This application is a divisional application of U.S. patent application Ser. No. 15/160,013, filed on May 20, 2016, which claims the benefit of U.S. Provisional Patent Application No. 62/168,770, filed May 30, 2015, U.S. Provisional Patent Application No. 62/183,300, filed Jun. 23, 2015, and U.S. Provisional Patent Application No. 62/284,812, filed Oct. 9, 2015, the disclosures of each of which are incorporated into this specification by reference in its entirety.

FIELD OF TECHNOLOGY

The present disclosure generally relates to high purity lithium and associated products. More specifically, for example, the present disclosure relates to highly purified lithium metal produced using a room temperature electrolytic process facilitated by a cell consisting of electrolytes and a membrane that selectively conducts only lithium ions to generate highly purified lithium and products incorporating the highly purified lithium metal. In an embodiment, the disclosed lithium metal has a purity of greater than 99.96 weight percent on a metals basis. Additionally the present disclosure also relates to continuous processes for obtaining lithium metal and cells for carrying out the process.

BACKGROUND

Lithium is a soft, silver-white metal belonging to the alkali metal group of chemical elements. Lithium is present in over fifty compounds and has two stable isotopes, Lithium-6 and Lithium-7. It is the lightest metal and the least dense solid element. Lithium is highly reactive and flammable, though it is the least reactive of the alkali metals. Since lithium only has a single valence electron that is easily given up to form a cation, it is a good conductor of heat and electricity. Lithium also has the highest electrochemical potential of all metals.

Because of its high reactivity, lithium does not occur freely in nature. Instead, lithium only appears naturally in compositions, usually ionic in nature, such as lithium carbonate. Therefore, lithium metal can be obtained only by extraction of lithium from compounds containing lithium.

The two most common ways of obtaining lithium are currently through extraction of lithium present in either spodumene or brine, producing carbonate. Lithium is then obtained from the lithium carbonate in two phases: (1) conversion of lithium carbonate into lithium chloride, and (2) electrolysis of lithium chloride using a high-temperature molten salt such as LiCl.

To convert lithium carbonate to lithium chloride, the lithium carbonate is heated and mixed with hydrochloric acid (typically 31% HCl) in an agitated reactor to generate lithium chloride, carbon dioxide and water as shown below:

$$Li_2CO_3(s)+2HCl(aq)\rightarrow 2LiCl(aq)+H_2O(aq)+CO_2(g)$$

The formed carbon dioxide is vented from the reactant solution. A small amount of barium chloride can be added to precipitate any sulfate. After filtering, the solution is evaporated to a saleable 40% LiCl liquid product. Potassium chloride can be added to provide a dry lithium chloride-potassium chloride (45% LiCl; 55% KCl) of decreased melting point (614° C. to approximately 420° C.). Then the lithium chloride-potassium chloride (45% LiCl; 55% KCl) in a molten pure and dry state can be utilized to produce lithium metal in a steel reaction cell using electrolysis as shown in the reactions below:

Cathode: $Li^+ + e^- \rightarrow Li$ metal

Anode: $Cl^- \rightarrow \frac{1}{2}Cl_2 + e^-$

Total: $2LiCl \rightarrow 2Li + Cl_2$

A conventional steel reaction cell has an exterior ceramic insulation and a steel rod on the bottom as a cathode. The anode is constructed of graphite, which slowly sloughs-off during processing. When the cell is heated, lithium metal accumulates at the surface of the cell wall and is then poured into ingots. Chlorine gas generated by the reaction is routed away. Typically, the electrolysis process is operated with a cell voltage from 6.7 V to 7.5 V, and the typical cell current is in the range of about 30 kA to 60 kA. The electrolytic processing consumes about 30 kWh to 35 kWh of electricity energy and about 6.2 to about 6.4 kg LiCl to produce one kilogram lithium metal with about 20% to 40% energy efficiency. Improvements to the molten salt electrolysis process have involved the selection of different types of electrolytic molten salts that allow for a decrease in operating temperatures.

For example, U.S. Pat. No. 4,156,635 to Cooper et al. describes an electrolytic process for the production of lithium using a lithium-amalgam electrode. The lithium is recovered from its molten amalgam using a fused-salt molten electrolyte consisting of a mixture of at least two alkali metal halides. The metal halides may include lithium iodide, lithium chloride, potassium iodide, and potassium chloride. U.S. Pat. No. 4,156,635 teaches that the lithium amalgam is produced by electrolysis of an aqueous solution of a lithium salt such as lithium hydroxide in the present of a mercury cathode. The lithium amalgam is then circulated between an aqueous cell containing the lithium salt solution and a fused-salt cell containing the molten electrolyte, and the lithium amalgam serves as a bipolar electrode.

Another low temperature technology involves electrolysis of brine to form chlorine at an anode and sodium hydroxide or potassium hydroxide via a series of cathode reactions. The formation of either of these hydroxides can involve the reduction of $Li^+$ to metal at a liquid mercury cathode, followed by reaction of the formed mercury amalgam with water. The process operates near room temperature with a lower voltage than required for the molten salt system.

U.S. Pat. No. 8,715,482 to Amendola et al. provides a system and process for producing lithium without a mercury electrode. The liquid metal alloy electrode system of U.S. Pat. No. 8,715,482 includes: an electrolytic cell comprising a liquid metal cathode and an aqueous solution wherein the aqueous solution containing lithium ion and at least an anion selected from sulfate, trifluoromethane sulfonate, fluorosulfonate, trifluoroborate, trifluoroacetate, trifluorosilicate and kinetically hindered acid anions, and wherein the lithium ion is produced from lithium carbonate. A heating system maintains temperature of the cell and liquid metal circulating systems higher than the melting point of the liquid metal cathode but lower than the boiling point of the aqueous solution. The reduced lithium from the electrolytic cell is extracted from the liquid metal cathode using a suitable extraction solution and a distillation system for isolating the lithium metal. This system is solid at room temperature and is less toxic than previous systems.

U.S. Pat. No. 6,770,187 to Putter et al. discloses another process that overcomes some of the high energy consumption and high temperature requirements of prior art processes. The process enables recycling of alkali metals from aqueous alkali metal waste, in particular, lithium from aqueous lithium waste. U.S. Pat. No. 6,770,187 provides an electrolytic cell comprising: an anode compartment which comprises an aqueous solution of at least one alkali metal salt, a cathode compartment, and an ion conducting solid composite that separates the anode compartment and the cathode compartment from one another, wherein that part of the surface of the solid electrolyte composite that is in contact with the anode compartment and/or that part of the surface of the solid electrolyte that is in contact with the cathode compartment has/have at least one further ion-conducting layer. The electrolyte used in U.S. Pat. No. 6,770,187 is water or water with organic solvent.

Lithium metal readily reacts with water to form hydrogen gas and lithium hydroxide. Because of its reactivity, lithium metal, once extracted from a lithium compound, is usually stored under cover of a hydrocarbon, often petroleum jelly. Though the heavier alkali metals can be stored in more dense substances, such as mineral oil, lithium metal is not dense enough to be fully submerged in these liquids. In moist air, lithium metal rapidly tarnishes to form a black coating of lithium hydroxide (LiOH and $LiOH.H_2O$), lithium nitride (LiN) and lithium carbonate ($Li_2CO_3$).

Because of lithium's high electrochemical potential, it is an important component of electrolytes and electrodes in batteries. For example, lithium metal is commonly used as an anode material in a lithium primary battery. Lithium metal is currently used as an anode material in two rechargeable batteries: a lithium sulfur battery developed by Sion Power Company and a lithium metal polymer battery used by the Bolloré Group. However, the lithium sulfur battery mentioned above requires a protective cover on the anode, and the lithium metal polymer battery technology utilizes a low capacity cell system specifically integrated into an electric vehicle. Mass adaptation of lithium metal anodes in rechargeable batteries has not yet been realized due to problems with dendrite formation.

Lithium metal anodes are particularly desirable for use in batteries, since batteries using a lithium metal anode have much higher energy densities than batteries using graphite or other conventional non-lithium anode materials. Lithium metal anodes have the highest specific capacity value of 3.86 Ah/g and energy density of 1470 Wh/Kg.

However, lithium metal produced by conventional lithium producing processes contains impurities that undesirably cause dendrite formation when the lithium metal is used as an anode in a rechargeable battery. The conventional process produces lithium foils with surface defects and cracks which serve as nucleation sites for dendrite growth For example, during charge and discharge cycling of the battery, impurities in the lithium metal cause lithium crystals (i.e., "dendrites") to emerge from the surface of the anode and spread across the electrolyte. In lithium polymer systems, dendrites begin forming at the electrode underneath the polymer/electrode interface prior to coming into contact with the electrolyte. In the same system, dendrites have also been observed on the uncycled lithium anode. Dendrite formation causes the battery to short-circuit, thereby increasing the temperature of the battery to potentially unsafe levels, resulting in thermal runaway or even death. Therefore, higher-purity lithium metal with a stable, uniform solid electrolyte interphase (SEI) layer that does not contain the impurities resulting from conventional lithium producing processes is desirable, and would result in a two-fold reduction of dendrite suppressing efforts, firstly by eliminating nucleation sites, and secondly by eliminating side reactions due to impurities.

Metallic lithium can also be used as a flux for welding or soldering to promote fusing of metals to eliminate oxide formation by absorbing impurities. Its fusing quality is important as a flux for producing ceramics, enamels and glass. Metallic lithium is also used in the metallurgical industry to form alloys containing lithium. High purity lithium metal is desirable in forming alloys to reduce the overall impurity level in the alloys. High purity lithium metal and alloys containing such high purity metal are also desirable as an improvement in currently available primary lithium batteries. Furthermore, increasing the concentration of lithium metal in an alloy, such as a lithium aluminum alloy, would result in an increased performance and lifespan for primary lithium batteries.

Lithium metal may also be used to make certain lithium compounds. For example, lithium oxide may be used as a flux for processing silica to glazes of low coefficients of thermal expansion, lithium carbonate ($Li_2CO_3$) may be used as a component in ovenware, and lithium hydroxide (LiOH) may be used as a strong base that can be heated with a fat to produce a lithium stearate soap. Lithium hydroxide monohydrate may be used as feedstock to produce a cathode material used in cylindrical cells, such as the Panasonic 18650 rechargeable lithium-ion battery. Notably, nickel cobalt aluminum (NCA) cathodes used in the cylindrical cells may require a high-purity LiOH. The cylindrical cells may be used in a battery pack. Lithium soap can be used to thicken oils and in the manufacture of lubricating greases. Lithium metal may also be used to form lithium fluoride. Due to its ultraviolet ("UV") transmission, lithium fluoride is used as a material in special UV optics. Lithium compounds are used in a wide variety of lithium battery electrolytes, for example $LiPF_6$, a common Lithium-ion battery electrolyte. Lithium salts such as lithium carbonate, lithium citrate and lithium orotate are also used in the pharmaceutical industry as mood stabilizers to treat psychiatric disorders such as depression and bipolar disorder. High purity lithium is desirable when making these lithium compounds in order to reduce the overall impurity level in the resulting compounds.

SUMMARY

There is a need for high purity lithium metal that does not contain the impurities typically present in lithium metal produced by conventional processes. Previous lithium producing systems have involved substantial capital and operating costs, and use and release noxious materials including mercury. There is therefore also a need for a direct and improved electrolysis process that requires reduced capital and operating costs in a system that effectively provides direct production of lithium metal.

In one non-limiting aspect, the present disclosure relates to high purity lithium metal that does not contain the impurities associated with conventional lithium producing processes. In an embodiment, the present disclosure provides a lithium metal product obtained using a selective lithium ion conducting layer. The lithium metal product includes a lithium metal having a purity of greater than 99.96 weight percent on a metals basis. The high purity lithium metal can be free of mercury and other nonconductive impurities that are present in lithium produced by conventional processes.

In an embodiment, the lithium metal is free of any metal impurities.

In an embodiment, the lithium metal has a purity of 100% weight without a solid electrolyte interphase (SEI) layer.

In an embodiment, the lithium metal has a stable uniform solid electrolyte interphase (SEI) layer with a skin depth less than 4 µm thick which can be customized for specific battery technologies by modifying the electrolyte.

In an embodiment, the lithium metal films are smooth, dendrite free, and uniform under scanning electron microscopy (SEM) images at 0.4 µm.

In an embodiment, the selective lithium ion conducting layer comprises an active metal ion conducting glass, glass-ceramic, or a glass-ceramic-polymer. In such an embodiment, the selective lithium ion conducting layer may include a lithium ion conductive barrier film.

In an embodiment, the lithium metal is coated onto a strip of material in a continuous strip coating process. The lithium-coated strip may be continuously fed into a system for producing a lithium compound such as lithium hydroxide.

In an embodiment, the lithium metal may be processed with deionized water to form lithium hydroxide and hydrogen, or lithium hydroxide monohydrate.

In an embodiment, the lithium metal is obtained by extracting lithium metal from a lithium salt using the selective ion conducting layer.

In an embodiment, a lithium metal electrode is provided. The lithium metal electrode includes lithium metal that is obtained by extracting lithium metal from a lithium salt using the selective ion conducting layer.

In an embodiment, a battery is provided and includes a cathode, an anode and an electrolyte. The anode comprises lithium metal that is obtained using a selective lithium ion conducting layer.

In an embodiment, a lithium metal compound is provided. The lithium metal compound includes lithium metal that is obtained using a selective lithium ion conducting layer.

In an embodiment, a lithium metal alloy is provided. The lithium metal alloy includes lithium metal that is obtained using a selective lithium ion conducting layer.

In an embodiment, the present disclosure provides a process of producing lithium hydroxide. The process includes extracting lithium metal from a lithium salt using a selective lithium ion conducting layer. The lithium metal is processed with deionized water to form lithium hydroxide and lithium hydroxide monohydrate.

In an embodiment, the present disclosure provides a lithium producing cell that includes a cell body, a sulfuric acid solution within the cell body, an anode within the cell body, an opposing and adjustable cathode moveable within the cell body, a catholyte on the cathode side of the cell, and a conductive glass-ceramic composite layer intercalated between the cathode and the electrolyte aqueous solution. The sulfuric acid solution contains lithium ion and an anion. The cell can include an insertion/retraction module connected to the cathode to adjustably control the cathode.

In an embodiment, the present disclosure provides a process for reducing impurities in lithium. The process includes providing a lithium ion source in a sulfuric acid solvent wherein lithium anion is dissolved in the solvent to form a lithium feed solution. An anode is provided in contact with the solution. A composite layer is provided transecting an axis of the cell body, the composite layer, comprising a lithium ion glass-ceramic. An adjustable cathode is moveable within the cell body cathode to a position apart from composite layer contact and suitable for electrolysis of lithium. A catholyte is provided on the cathode side of an electrolytic cell. An ionizing electric current is provided to the electrolytic cell, thereby producing lithium metal at the cathode.

In an embodiment, the present disclosure provides a process for separating Lithium-6 and Lithium-7 isotopes from lithium metal. The process includes providing an electrolytic cell comprising an organic aqueous solution. A nonaqueous electrolyte and a selective lithium ion conducting membrane are provided. The Lithium-6 and Lithium-7 isotopes in the lithium metal are caused to pass through the membrane at different velocities. At least one of the Lithium-6 and Lithium-7 isotopes are captured.

In an embodiment, enriched Lithium-6 and Lithium-7 isotopes are provided. The enriched isotopes are obtained using an electrolytic cell comprising an organic aqueous solution, a nonaqueous electrolyte and a selective lithium ion conducting membrane to separate the lithium isotopes.

In an embodiment, a lithium metal containing product is provided. The lithium metal comprises, in parts per million by weight: less than 0.6 silver (Ag), less than 2 aluminum (Al), less than 0.2 arsenic (As), less than 0.1 gold (Au), less than 0.4 boron (B), less than 0.4 barium (Ba), less than 0.5 beryllium (Be), less than 0.1 bismuth (Bi), less than 4 calcium (Ca), less than 0.5 cadmium (Cd), less than 0.4 cerium (Ce), less than 0.4 cobalt (Co), less than 0.4 chromium (Cr), less than 0.4 cesium (Cs), less than 0.4 copper (Cu), less than 0.4 dysprosium (Dy), less than 0.4 erbium (Er), less than 0.5 europium (Eu), less than 0.7 iron (Fe), less than 0.4 gallium (Ga), less than 0.4 gadolinium (Gd), less than 0.3 germanium (Ge), less than 0.2 hafnium (Hf), less than 0.3 mercury (Hg), less than 0.3 holmium (Ho), less than 0.5 indium (In), less than 0.2 iridium (Ir), less than 0.5 potassium (K), less than 0.4 lanthanum (La), less than 0.1 lutetium (Lu), less than 5 magnesium (Mg), less than 0.3 manganese (Mn), less than 0.4 molybdenum (Mo), less than 0.3 niobium (Nb), less than 0.4 neodymium (Nd), less than 0.9 nickel (Ni), less than 0.4 osmium (Os), less than 10 phosphorus (P), less than 0.1 lead (Pb), less than 0.5 palladium (Pd), less than 0.4 praseodymium (Pr), less than 0.2 platinum (Pt), less than 0.4 rubidium (Rb), less than 0.1 rhenium (Re), less than 0.3 rhodium (Rh), less than 0.4 ruthenium (Ru), less than 13 sodium (Na), less than 19 sulfur (S), less than 0.3 antimony (Sb), less than 0.5 scandium (Sc), less than 1 selenium (Se), less than 69 silicon (Si), less than 0.5 samarium (Sm), less than 0.7 tin (Sn), less than 0.5 strontium (Sr), less than 0.1 tantalum (Ta), less than 0.3 terbium (Tb), less than 0.4 tellurium (Te), less than 0.1 thorium (Th), less than 0.4 titanium (Ti), less than 0.1 thallium (Tl), less than 0.2 thulium (Tm), less than 0.1 uranium (U), less than 0.5 vanadium (V), less than 0.2 tungsten (W), less than 0.4 yttrium (Y), less than 0.2 ytterbium (Yb), less than 1 zinc (Zn), and less than 0.3 zirconium (Zr). Thus, the total impurities in the lithium metal are less than 0.002 weight percent.

In an embodiment, the disclosed lithium metal has a purity of greater than 99.998 weight percent on a metals basis. In an embodiment, the high purity lithium metal has no impurities above the minimum detectable limit of the inductively coupled plasma mass spectrometry (ICP-MS) method. In an embodiment, the high purity lithium metal has no impurities.

An advantage of the present disclosure is to provide a lithium metal product having an improved lithium metal purity. By using a selective lithium ion conducting membrane to extract lithium metal from a lithium salt, the impurities present in conventional lithium producing processes are not passed to the final lithium metal product.

Another advantage of the present disclosure is to provide an electrode containing a lithium metal anode with an improved purity of lithium and a battery containing such an electrode. By providing a lithium metal anode having a high purity, the concentration of the active material is increased resulting in higher capacity, longer cycle life and energy density. The anode can be used in batteries without causing or contributing to dendrite formation, therefore mitigating catastrophic consequences.

Still another advantage of the present disclosure is to provide lithium alloys and lithium compounds containing a lithium metal having an improved purity. By providing a lithium metal compound or alloy having a higher purity, the final alloy or compound can desirably have an improved overall purity.

Another advantage of the present invention is to provide a process that consumes less energy. Traditional electrolytic processing consumes about 30 kWh to 35 kWh of electrical energy to produce one kilogram lithium metal with about 20% to 40% energy efficiency. The presently disclosed process uses only 8 kWh of electrical energy to produce one kilogram lithium metal with 90% to 100% efficiency.

Another advantage of the present invention is to provide a number of products that can contain the lithium metal of the present disclosure. By way of an example, the products include a camera, a camcorder, a computer, a cellular phone, a personal digital assistant, a clock, a watch, a car key, a sensor, a remote control, an audio device, an audiovisual device, an oceanographic device, a capacitor, a metacapacitor, a supercapacitor, an automobile, an airplane, a drone, a spacecraft, a satellite, an implantable medical device, a consumer product, a primary battery, and a rechargeable battery.

Additional features and advantages are described herein, and will be apparent from the following Detailed Description and the figures.

BRIEF DESCRIPTION OF THE FIGURES

FIG. 1 shows a schematic elevation view of a lithium producing cell structure used to produce a high purity lithium metal product in an embodiment of the present disclosure.

FIG. 2 is an enlarged partial view of the lithium producing cell structure of FIG. 1.

DETAILED DESCRIPTION

Figure 3A:
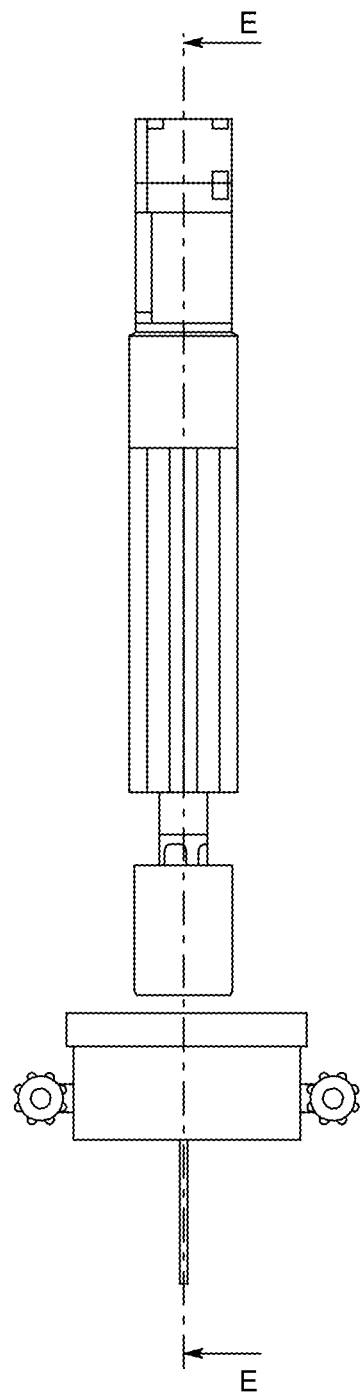
FIG. 3A is a schematic elevation view of a lithium producing cell used to produce a high purity lithium metal product in another embodiment of the present disclosure.
Figure 3B:
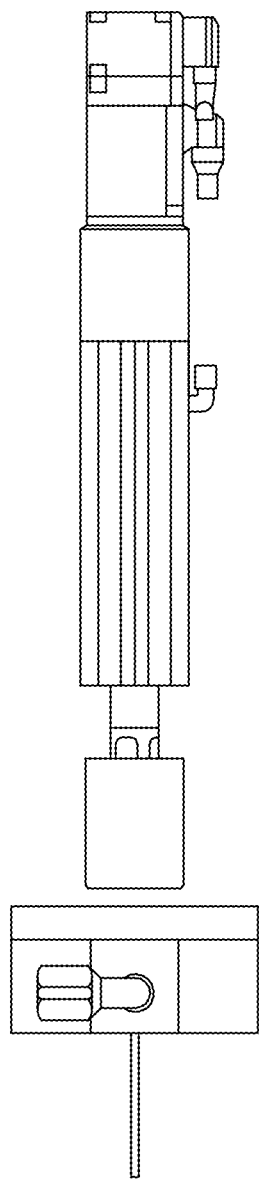
FIG. 3B is a side view of the lithium producing cell of FIG. 3A.
Figure 3C:
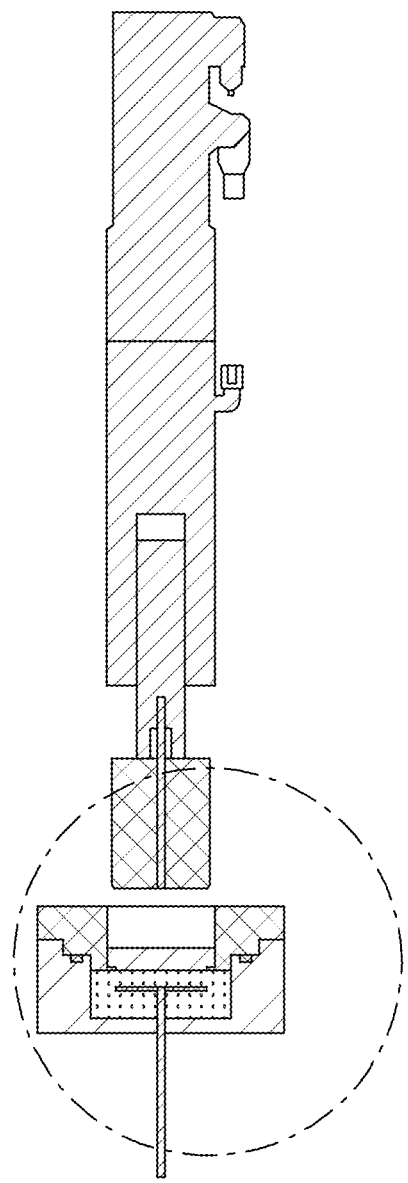
FIG. 3C is a section view taken along E-E of FIG. 3A.

The present disclosure generally relates to high purity lithium and associated products. Additionally the present disclosure also relates to continuous processes for obtaining lithium metal and cells for carrying out the process.

According to certain non-limiting embodiments, the present disclosure provides an extractable/insertable cathode separated from lithium ion rich solution by a selectively permeable barrier composite. The composite comprises a lithium ion conductive glass-ceramic (LiC-GC) layer. The lithium ion conductive glass-ceramic (LiC-GC) composite allows for direct production of lithium metal from solution and direct deposition of lithium metal onto a clean cathode, without need for an additional extraction process.

According to certain non-limiting embodiments, the present disclosure provides a system including an electrolyte feed system that provides a lithium ion rich electrolyte to the electrolytic cell, and an electrolytic cell to move lithium metal from a water-based lithium ion solution through the lithium ion conductive glass-ceramic (LiC-GC) membrane.

According to certain non-limiting embodiments, the present disclosure provides a method to remove the lithium metal from the cell and then continue production with that cell, and a method to package lithium metal. The method can be part of a continuous lithium metal production process or as a batch process.

According to certain non-limiting embodiments, the present disclosure provides a high purity lithium metal that is obtained using a selective lithium ion conducting layer and products containing the high purity lithium metal. The high purity lithium metal can be extracted from lithium carbonate or other naturally occurring sources of lithium. The lithium metal has high purity on a metals basis due to the selective conduction of lithium ions across the lithium ion conducting layer. The high purity lithium metal may be used to produce lithium hydroxide then evaporated to produce lithium hydroxide monohydrate.

A high purity lithium metal according to an embodiment may be produced using a cell as shown in FIGS. 1 and 2. In FIGS. 1 and 2, the electrolytic cell 10 includes an upper section 12 and lower section 14. The cathode 16 transposes an axis of cell 10, advancing as an electrolysis reaction takes place in electrolyte 18 above the cathode 16, through a lithium ion conductive glass-ceramic-barrier film (LiC-GC-BF) composite layer 28. When potential is applied to the system, lithium metal builds up on the moving cathode 16 below the composite layer 28. Anode 20 is provided in the cell upper section 12. The cell section 12 above the cathode 10 is loaded with electrolyte 18 via inlet 22, electrolysis proceeds and spent electrolyte is discharged via outlet 24. The cathode 16 is in contact with the electrolyte 18 through the composite layer 28 intercalated between the cathode 16 and electrolyte 18.

The composite layer 28 comprises a lithium ion conductive glass-ceramic (LiC-GC) layer 30 adjacent the electrolyte 18 and a lithium ion conductive barrier film (Li—BF) 32 interposed between the ceramic layer 30 and cathode 16. The barrier layer 32 and glass-ceramic layer 30, together, composite 28, isolates forming lithium at cathode 16 from electrolyte 18. Shaft 26 advances the cathode 16 and composite 28 as lithium metal is formed and deposited through the composite layer 28 onto the advancing cathode 16. The lithium metal produced at the solid cathode 16 can be drawn off as a pure metallic phase to form a high purity lithium product.

Alternatively, in a non-limiting embodiment, the lithium metal produced at the cathode 16 allows for flexible deposition onto a myriad of different substrates that can easily be integrated into some battery manufacturers' production processes, thereby streamlining the processes. Examples include a copper foil, a graphite coated copper foil (capacitor), ($Li_7La_3Zr_2O_2$ (LLZO) Garnet), onto Cu by atomic layer deposition (ALD), onto a 3D current collector/substrate, a grooved piece of Cu or appropriate substrate, or a rotating cathode can deposit micron sized rods of lithium with a stable uniform solid electrolyte interphase (SEI) layer onto the substrates used in microbatteries in a continuous system.

Alternatively, the lithium metal produced at the cathode 16 may be used to produce lithiated substrates, such as a carbon anode lithiated with high purity lithium rather than deposited lithium.

Alternatively, the lithium metal produced at the cathode 16 may be directly coated onto a strip of material in a continuous strip coating process. The lithium-coated strip may then be continuously fed into a system for producing a lithium compound such as lithium hydroxide monohydrate. Specifically, the high purity lithium metal may be mixed with deionized water to form lithium hydroxide and hydrogen according to the following reaction:

$$2Li+2H_2O \rightarrow 2LiOH+H_2$$

The hydrogen produced in this lithium hydroxide formation process may be vented off, burned off or stored. For example, the hydrogen may be burned off in air to form water, or simply vented to the atmosphere where it will combine with oxygen to form water vapor. Alternatively, the hydrogen may be captured in capsules or cartridges. The capsules or cartridges containing hydrogen may be used as rechargeable cartridges in a fuel cell battery for consumer electronics.

Alternatively, to produce lithium hydroxide monohydrate, the cell can be modified to be used as a two (or three) chamber electrolyzer. The aqueous solution remains $Li_2CO_3$ and sulfuric acid by a simple metathesis reaction which dissociates the $Li_2CO_3$. Lithium ions are passed through the composite layer 28 into catholyte 18 which is then processed into LiOH solution. Alternatively, the obtained LiOH solution is delivered to the stage of evaporation. Dehydration to produce LiOH monohydrate can be accomplished by heating the high purity LiOH solution in a vacuum or under the cover of an inert gas at a temperature of approximately ambient temperatures or slightly above ambient temperatures. The dried crystalline lithium hydroxide monohydrate ($LiOH.H_2O$) is then packaged in inert atmosphere.

In another embodiment a lithium hydroxide solution is the catholyte. As lithium is processed through the membrane, both the concentration of lithium hydroxide and the solution pH increases. Periodically, portions of the LiOH electrolyte solution can be bled off and dehydrated to lithium hydroxide monohydrate, replacing the solution removed with deionized water to return it to the original concentration; a continuous control, maintaining a specific concentration in the circulating catholyte, could also be used. In such cases, operating temperature can be raised (though remaining below the boiling point of the LiOH electrolyte) to increase conductivity of the membrane.

When using an aqueous electrolyte on both sides of the membrane of the cell, membranes not exhibiting extremely low moisture permeability can be used. As such, a polyethylene oxide composite, garnet, or other suitable membranes can be used for lithium hydroxide processing, or for any other aqueous catholyte-aqueous anolyte system.

The benefits of having a higher purity LiOH solution is advantageous in regards to reducing the number of purification steps resulting in energy saving in evaporation or a solution of conversion of LiOH in production of $LiOH.H_2O$.

The lithium hydroxide monohydrate may be used as cathode material in a lithium-ion battery. High purity lithium hydroxide is used in nickel cobalt aluminum (NCA) cathodes. The lithium hydroxide and lithium hydroxide monohydrate may also be used as a heat transfer medium, a storage-battery electrolyte, a material in ceramics, or a material in a cement formulation. The lithium hydroxide and lithium hydroxide monohydrate may also be used in breathing gas purification systems for spacecraft, submarines and rebreathers to remove carbon dioxide from exhaled gas to produce lithium carbonate and water according to one of the following reactions:

$$2LiOH.H_2O+CO_2 \rightarrow Li_2CO_3+2H_2O \text{ or}$$

$$2LiOH+CO_2 \rightarrow Li_2CO_3+H_2O$$

The lithium hydroxide and lithium hydroxide monohydrate produced using the high purity lithium metal advantageously contains fewer impurities than lithium hydroxide and lithium hydroxide monohydrate produced using conventional lithium metal. For example, because the lithium hydroxide is formed using the high purity lithium metal, and deionized water, the lithium hydroxide does not contain mercury or nonconductive impurities associated with lithium metal formed using conventional processes. Furthermore, the lithium hydroxide produced using the high purity lithium metal has a higher concentration of lithium than lithium hydroxide and lithium hydroxide monohydrate currently on the market. Therefore, when the lithium hydroxide produced using the high purity lithium metal is used as a feedstock for a cathode material in a lithium-ion battery, the active material is increased and the energy density and performance of the lithium-ion battery are enhanced.

Conventional methods of producing lithium hydroxide and lithium hydroxide monohydrate are complex and costly, requiring a large number of purification steps, and the resulting purity levels are low. Therefore, by using the high purity lithium metal to produce lithium hydroxide and lithium hydroxide monohydrate, the process costs will be lowered and the supplies of lithium hydroxide and lithium hydroxide monohydrate may be increased.

Suitable feed to the cell includes water-soluble lithium salts including but not limited to $Li_2CO_3$ (lithium carbonate) and LiCl. Lithium carbonate ($Li_2CO_3$) is the most readily available lithium salt, being relatively inexpensive and is a preferred lithium source. To improve solubility, the lithium salt is dissolved in hydrated acid such as sulfuric acid and used as electrolyte 18 in the electrolytic cell.

In an embodiment, recycling lithium feed from lithium batteries may, for example, be accomplished by addition of sulfuric acid. The slurry of recycled lithium battery feed stock is placed into electrolyte 11 and processed with sulfuric acid to dissociate the solution. Current is applied to the cell, and the lithium ions pass through the lithium ion conductive glass-ceramic (LiC-GC) layer into the catholyte for the high purity lithium metal to be harvested at the cathode, exactly like the original process.

Specifically, a sulfuric acid electrolyte may be used to disassociate lithium carbonate, placing the lithium ions into solution for processing and venting off the carbonate portion without it entering into solution. By disassociating the lithium carbonate and only placing the lithium ions into solution, the electrolyte solution remains stable and does not build up a concentration of the non-lithium ion portion of the feed stock. Lithium carbonate can be continuously fed into a tank outside of the electrolytic cell, venting off the $CO_2$ gas released by the sulfuric acid electrolyte. The acid electrolyte does not need to be disposed of or replenished, lithium carbonate can be continuously added to a feed tank, venting off $CO_2$ and harvesting lithium metal from the cathode. This can be continuously operated or conducted as a batch process.

Cathode 16 is characterized by the intercalated composite lithium ion conductive glass-ceramic (LiC-GC)/lithium ion conductive barrier film (Li—BF) 28, e.g., the composite 28 is inserted or interposed between the cathode 16 and electrolyte 18. If both the catholyte and anolyte are aqueous, the membrane would not need to be LiC-GC; the membrane could be a polyethylene oxide composite, garnet, or other suitable membranes that allow moisture permeation. The cathode 16 can be characterized as "transpositioning" meaning the cathode advances along an axis of the cell 10 to transpire produced lithium through the composite 28 and to isolate cathode-deposited lithium. The cathode comprises a suitable material that is non-reactive with lithium metal and the composite layer. The lithium ion conductive glass-ceramic (LiC-GC)/lithium ion conductive barrier film (Li—BF) composite layer is a stationary barrier between the anode compartment and the lithium metal forming on the cathode. The cathode moves to accommodate the continuously thickening layer of lithium metal on the cathode.

The substantially impervious selective lithium-ion conducting (LiC-GC) layer 30 can be an active metal ion conducting glass or glass-ceramic (e.g., a lithium ion conductive glass-ceramic that has high active metal ion conductivity and stability to aggressive electrolytes and compounds including water that vigorously react with lithium metal). Suitable materials are substantially impervious, ionically conductive, and chemically compatible with aqueous electrolytes, or other electrolytes (catholyte), and/or cathode materials that would otherwise adversely react with lithium metal. Such glass or glass-ceramic materials are substantially gap-free, non-swellable and are inherently ionically conductive (i.e., they do not depend on the presence of a liquid electrolyte or other agent for their ionically conductive properties). Suitable glass or glass-ceramic materials also have high ionic conductivity, at least $10^{-7}$ S/cm, generally at least $10^{-6}$ S/cm, for example at least $10^{-5}$ S/cm to $10^{-4}$ S/cm, and as high as $10^{-3}$ S/cm or higher so that the overall ionic conductivity of the multi-layer protective structure is at least $10^{-7}$ S/cm and as high as $10^{-3}$ S/cm or higher. The thickness of the layer is preferably about 0.1 to 1000 microns, or, where the ionic conductivity of the layer is about $10^{-7}$ S/cm, about 0.25 to 1 micron, or, where the ionic conductivity of the layer is between about $10^{-4}$ to about $10^{-3}$ S/cm, about 10 to 1000 microns, preferably between 1 and 500 microns, and more preferably between 50 and 250 microns, for example, about 150 microns.

For processes using an aqueous electrolyte on both sides of the membrane of the cell, permeable membranes are suitable.

Examples of the lithium ion conductive glass-ceramic (LiC-GC) layer 30 include glassy or amorphous metal ion conductors, such as a phosphorus-based glass, oxide-based glass, phosphorus-oxynitride-based glass, sulfur-based glass, oxide/sulfide-based glass, selenide-based glass, gallium-based glass, germanium-based glass or boracite glass (such as are described D. P. Button et al., Solid State Ionics, Vols. 9-10, Part 1, 585-592 (December 1983); ceramic active metal ion conductors, such as lithium beta-alumina, sodium beta-alumina, Li superionic conductor (LISICON), Na superionic conductor (NASICON), and the like; or glass-ceramic active metal ion conductors. Specific examples include LiPON (nitrided lithium phosphate), $Li_3PO_4$, $Li_2S$, $SiS_2$, $Li_2S$, $GeS_2$, $Ga_2S_3$ and $Li_2O$. Examples of permeable membranes suitable for processes using aqueous electrolytes on both sides of the cell include polyethylene oxide composites and garnet.

Suitable lithium ion conductive glass-ceramic (LiC-GC) materials include a lithium ion conductive glass-ceramic having the following composition in mol percent: $P_2O_5$ 26-55%; $SiO_2$ 0-15%; $GeO_2+TiO_2$ 25-50% (in which $GeO_2$ 0-50%; $TiO_2$ 0-50%); $ZrO_2$ 0-10%; $M_2O_3$ 0-10%; $Al_2O_3$ 0-15%; $Ga_2O_3$ 0-15%; $Li_2O$ 0-25%; and containing a predominant crystalline phase comprising $Li_{1+x}(M, Al, Ga)x$ $(Ge_{1-y}Ti_y)_{2-x}(PO4)_3$ where $x \leq 0.8$ and $0 \leq y \leq 1.0$, and where M is an element selected from the group consisting of Nd, Sm, Eu, Gd, Tb, Dy, Ho, Er, Tm and Yb, and/or $Li_{1+x+y}Q_xTi_{2-x}Si_3P_{3-y}O_{12}$, where $0 < x \leq 0.4$ and $0 < y \leq 0.6$, and where Q is Al or Ga. Other examples include $Li_2O-11Al_2O_3$, $Na_2O-11Al_2O_3$, $(Na, Li)_{1+x}Ti_{2-x}Al_x(PO_4)_3$ ($0.6 \leq x \leq 0.9$) and crystallographically related structures, $Na_3Zr_2Si_2PO_{12}$, $Li_3Zr_2Si_2PO_4$, $Na_5ZrP_3O_{12}$, $Na_5TiP_3O_{12}$, $Na_3Fe_2P_3O_{12}$, $Na_4NbP_3O_{12}$, $Li_5ZrP_3O_{12}$, $Li_5TiP_3O_{12}$, $Li_5Fe_2P_3O_{12}$, $Li_4NbP_3O_{12}$, $Li_7La_3Zr_2O_2$ (LLZO), and combinations thereof, optionally sintered or melted. Suitable ceramic ion active metal ion conductors are described, for example, in U.S. Pat. No. 4,985,317 to Adachi et al. Suitable material also includes polymer composites of the above. Suitable material also includes membranes allowing moisture permeation, including polyethylene oxide composite and garnet.

Suitable lithium ion conductive glass-ceramic (LiC-GC) materials include a product from Ohara, Inc. (Kanagawa, JP), trademarked LIC-GC™, LISICON, $Li_2O$—$Al_2O_3$—$SiO_2$—$P_2O_5$—$TiO_2$ (LATP). Suitable material with similarly high lithium metal ion conductivity and environmental/chemical resistance are manufactured by Ohara and others. See, for example, Inda, DN20100113243, now U.S. Pat. No. 8,476,174. U.S. Pat. No. 8,476,174 discloses a glass-ceramic comprising at least crystallines having a having a $LiTi_2P_3O_{12}$ structure, the crystallines satisfying $1 < I_{4113}/I_{4104} \leq 2$, wherein $I_{4104}$ is the peak intensity assigned to the plane index 104 ($2\theta=20$ to $21°$), and $I_{4113}$ is the peak intensity assigned to the plane index 113 ($2\theta=24$ to $25°$) as determined by X-ray diffractometry. Suitable material also includes membranes allowing moisture permeation, including polyethylene oxide composite and garnet.

The lithium ion conductive glass-ceramic (LiC-GC) layer 30 selectively allows only lithium ions to flow. Therefore, the resulting lithium metal produced using electrolytic cell 10 has a high purity. The inventor believes that the resulting lithium metal has a purity of nearly 100% and at least greater than 99.9% on a metals basis.

The lithium ion conductive barrier film (Li—BF) 32 is a lithium metal ion conductive film or coating with high lithium metal ion conductivity. The lithium ion conductive barrier film (Li—BF) 32 is a lithium metal ion conductive film or coating with high lithium metal ion conductivity, typically 1.0 mS/cm to 100 mS/cm. A high lithium ion transference number ($t_+$) is preferred. Low $t_+$ Li$^+$ electrolytes will hinder performance by allowing ion concentration gradients within the cell, leading to high internal resistances that may limit cell lifetime and limit reduction rates. Transference numbers between $t_+$=0.70 and $t_+$=1.0 are preferred. The lithium ion conductive barrier film is non-reactive to both lithium metal and the lithium-ion conductive glass-ceramic (LiC-GC) material.

The lithium ion conductive barrier film (Li—BF) 32 may be an active metal composite, where "active metals" include lithium, sodium, magnesium, calcium, and aluminum used as the active material of batteries. Suitable lithium ion conductive barrier film (Li—BF) material includes a composite reaction product of active metal with $Cu_3N$, active metal nitrides, active metal phosphides, active metal halides, active metal phosphorus sulfide glass, and active metal phosphorous oxynitride glass ($Cu_3N$, $L_3N$, $Li_3P$, LiI, LiF, LiBr, LiCl and LiPON). The lithium ion conductive barrier film (Li—BF) material must also protect against dendrites forming on the cathode from coming in contact with the lithium ion conductive glass-ceramic (LiC-GC) material. This may be accomplished by creating physical distance between the cathode and the lithium ion conductive glass-ceramic (LiC-GC) and/or providing a physical barrier that the dendrites do not penetrate easily. One preferred lithium ion conductive barrier film (Li—BF) is a physical organogel electrolyte produced by in situ thermo-irreversible gelation and single ion-predominant conduction as described by Kim et al. in Scientific Reports (article number: 1917 doi: 10.1038/srep01917). This electrolyte has $t_+$=0.84 and conductivity of 8.63 mS/cm at room temperature. This organogel electrolyte can be set up in a porous membrane to provide additional structure and resistance to dendrite penetration. Typical porous membrane thickness is 1 μm to 500 μm, for example 20 μm. Acceptable porous membranes include Hipore™ polyolefin flat-film membrane by Asahi Kasei E-materials Corporation.

Figure 3D:
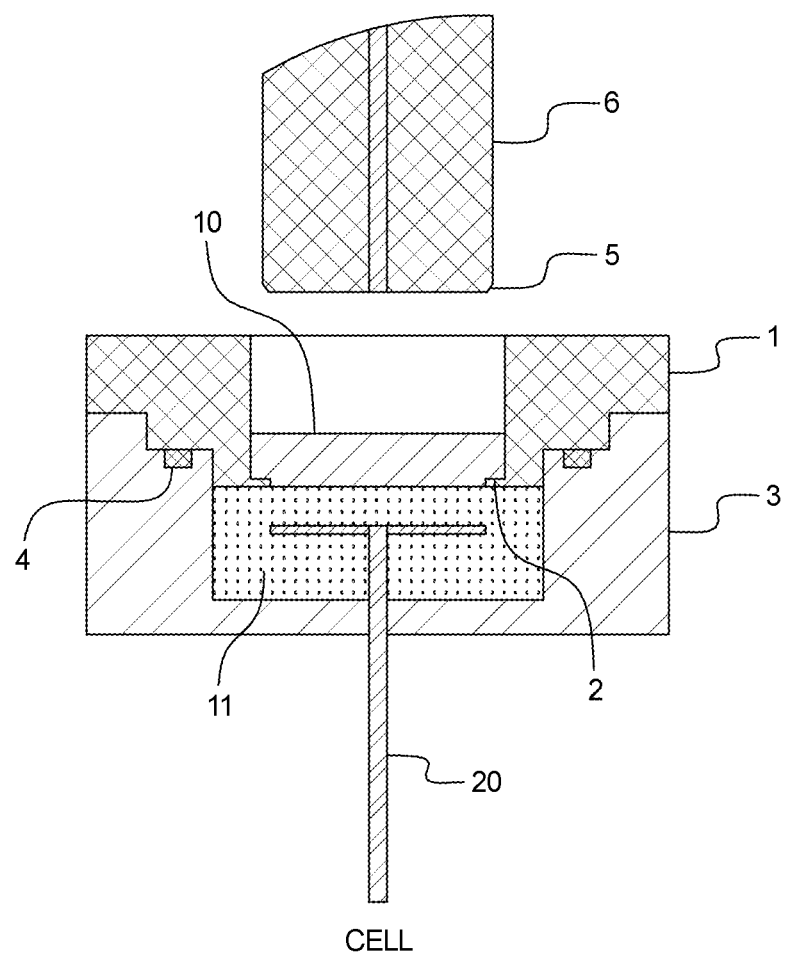
FIG. 3D is an enlarged partial view of the lithium producing cell of FIG. 3C.
Figure 3E:
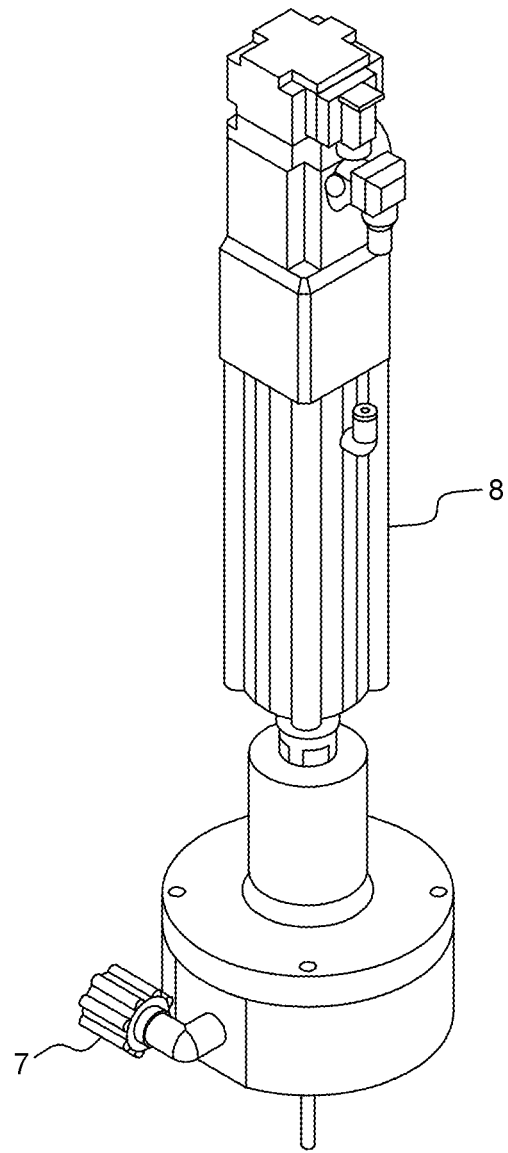
FIG. 3E is a rear perspective view of the lithium producing cell of FIG. 3A.

A high purity lithium metal according to another embodiment may be produced using a cell as shown in FIGS. 3A-3E. When producing lithium metal, the membrane should be substantially impervious to moisture. The cell of FIGS. 3A-3E shows a production system and process wherein high purity lithium metal is extracted from a lithium ion containing electrolyte 11. The electrolytic cell of FIG. 3D shows a sleeve 1 and a cell body 3. In an embodiment, the cell body 3 can be made of a suitably rigid material such as polypropylene. The high purity lithium and associated products and processes described herein are not limited in this regard. The cell includes a movable cathode 5 that transposes an axis of the cell body 3 and can be positioned to variable heights above a lithium ion conductive glass-ceramic (LiC-GC) membrane 2. With the cathode 5 positioned in catholyte 10 above the lithium ion conductive glass-ceramic (LiC-GC) membrane 2, ion transfer can occur through a lithium ion conductive glass-ceramic (LiC-GC) composite layer onto the cathode 5. The anode 20' in this embodiment is provided in a lower portion of cell body 3, and can be made of stainless steel for sulfuric acid resistance. Alternatively, the anode 20' can be made from titanium or niobium coated with platinum, gold, or ruthenium. The portion of cell body 3 below the lithium ion conductive glass-ceramic (LiC-GC) membrane 2 is loaded with lithium ion containing electrolyte via inlet 20, electrolysis proceeds and spent electrolyte is discharged via outlet 21. Lithium ions are conducted from the lithium ion containing electrolyte 11, through the lithium ion conductive glass-ceramic (LiC-GC) membrane 2 and lithium ion conducting catholyte 10 to the cathode 5.

The cathode 5 is spaced apart from the lithium ion conductive glass-ceramic (LiC-GC) membrane 2 intercalated between the cathode 5 and electrolyte 11. The composite layer comprises a lithium ion conductive glass-ceramic layer (LiC-GC) 2 interposed between the lithium ion containing electrolyte 11 and the lithium ion conducting catholyte 10. The glass-ceramic layer 2 and the cathode spacing isolates lithium forming at cathode 5 from electrolyte 11. Cathode support 6 is driven by a servo motor and advances the cathode 5 as required to maintain spacing between lithium metal formed on the cathode and the lithium ion conductive glass-ceramic (LiC-GC) membrane 2, and also to withdraw the cathode for lithium metal removal. The lithium metal produced at the solid cathode 5 can be drawn off as a pure metallic phase.

Suitable cell components for the cell of FIG. 3 include many of the same components as the embodiment of the lithium producing cell structure described above in connection with FIG. 1, and also cell components described in US20130004852. Suitable feed to the cell of FIG. 3 includes the same materials disclosed for the embodiment of the lithium producing cell structure described above in connection with FIG. 1, specifically water-soluble lithium salts including but not limited to $Li_2CO_3$ (lithium carbonate) and LiCl. To improve solubility, as with the embodiment of the lithium producing cell structure described above in connection with FIG. 1, the lithium salt is dissolved in hydrated acid such as sulfuric acid and used as electrolyte 11 in the cell of FIG. 3. The acid electrolyte does not need to be disposed of or replenished, lithium carbonate can be continuously added to a feed tank, venting off $CO_2$ and harvesting lithium metal from a cathode. This can be continuously operated or conducted as a batch process.

Cathode 5 is characterized by the intercalated lithium ion conductive glass-ceramic (LiC-GC) membrane 2 inserted or interposed between the cathode 5 and electrolyte 11. The cathode 5 can be characterized as "transpositioning" meaning the cathode advances along an axis of the cell body 3 to transpire produced lithium through the catholyte 10 and to isolate cathode-deposited lithium. The cathode comprises a suitable material that is nonreactive with lithium metal and the composite layer. The lithium ion conductive glass-ceramic (LiC-GC) membrane 2 is a stationary barrier between the electrolyte 11 in the anode compartment and the catholyte 10 on the cathode side of the cell, allowing only lithium ion conduction through the membrane. The cathode 5 moves to position the cathode at the proper distance from the lithium ion conductive glass-ceramic (LiC-GC) membrane 2 during deposition, and retracts to allow deposited lithium metal to be harvested.

The selective lithium ion conductive glass-ceramic (LiC-GC) membrane 2 is a lithium ion conductive glass-ceramic layer. Suitable materials for the glass-ceramic layer include the same materials for the lithium ion conductive glass-ceramic (LiC-GC) layer 30 of the embodiment of the lithium producing cell structure described above in connection with FIG. 1.

For example, suitable materials for the glass-ceramic layer are electrically insulating, substantially impervious, ionically conductive, and chemically compatible with aqueous electrolytes, or other electrolytes (catholytes), and/or cathode materials that would otherwise adversely react with lithium metal. Such materials also have high ionic conductivity, at least $10^{-7}$ S/cm, generally at least $10^{-6}$ S/cm, for example at least $10^{-5}$ S/cm to $10^{-4}$ S/cm, and as high as $10^{-3}$ S/cm or higher, so that the overall ionic conductivity of the multi-layer protective structure is at least $10^{-7}$ S/cm and as high as $10^{-3}$ S/cm or higher. The thickness of the layer is preferably about 0.1 to 1000 microns, or, where the ionic conductivity of the layer is about $10^{-7}$ S/cm, about 0.25 to 1 micron, or, where the ionic conductivity of the layer is between about $10^{-4}$ S/cm to about $10^{-3}$ S/cm, about 10 to 1000 microns, preferably between 1 and 500 microns, and more preferably between 50 and 250 microns, for example, about 150 microns.

A lithium ion conducting catholyte 10 must be present between the cathode 5 and lithium ion conductive glass-ceramic (LiC-GC) membrane 2 to allow conduction of lithium ions to the cathode 5 from the electrolyte 11. This can be a simple lithium battery electrolyte such as a mixture of ethylene carbonate ("EC"), dimethyl carbonate ("DMC") and an electrolyte salt such as lithium hexafluorophosphate (LiPF$_6$), a mixture of dimethyl carbonate and lithium hexafluorophosphate (DMC-LiPF$_6$). an Ionic Liquid TFSI (trifluoromethanesulfonyl-imide)-based electrolyte such as N-butyl-N-methylpyrrolidinium bis(trifluoromethanesulfonyl)imide (Pyr$_{14}$TFSI), 1,3-dioxolane ethylene glycol methylene ether, formaldehyde ethylene acetal, a solution of LLZO (Li$_7$La$_3$Zr$_2$O$_2$) and Ionic Liquid trifluoromethane-sulfonyl-imide, Li bis(trifluoromethanesulfonyl)imide (LiTFSI) in 1-ethyl-3-methylimidazolium-bis(trifluoromethylsulfonyl)imide (EMI-TFSI), ether based electrolytes, anhydrous dioxolane with a small amount of BHT (butylated hydroxy toluene). In an embodiment, 1 M lithium bis (trifluoromethanesulphonyl)imide (LiTFSI) in 1,3-dioxolane and 1,2-dimethoxyethane (volume ratio 1:1) can be used with 1% lithium nitrate (LiNO$_3$) and 100 mM Li$_2$S$_8$ additives as the electrolyte. The presence of LiNO$_3$ and Li$_2$S$_8$ helps in the formation of a stable solid electrolyte interphase (SEI) on the lithium metal collecting cathode. Tetraglyme and Dioxolane combinations are also candidates. A more complex lithium ion conducting barrier film (Li—BF) is also a candidate. The use of a simple liquid electrolyte compatible with lithium metal greatly simplifies cell assembly and harvesting of deposited lithium as compared with the process disclosed in U.S. patent application Ser. No. 14/328,613. With the cell properly constructed (cathode 5 facing up) the liquid electrolyte can be poured into the space above the lithium ion conductive glass-ceramic (LiC-GC) membrane 2, on the cathode side of the cell, and the cathode simply lowered into the electrolyte to perform deposition, or withdrawn from the electrolyte to harvest deposited metal.

The electrolyte can be modified in the catholyte to produce a desired solid electrolyte interphase (SEI) layer, or none at all.

A lithium ion conductive film (Li—BF) 32 can be present. However, the cathode spacing aspect of the present disclosure can eliminate this element. If present, the conductive barrier film is a lithium metal ion conductive film with high lithium metal ion conductivity. Suitable lithium ion conductive barrier films (Li—BF) include the same materials disclosed for lithium ion conductive barrier film (Li—BF) 32 of the embodiment of the lithium producing cell structure described above in connection with FIG. 1.

In the process using the cell of FIG. 3, anode and cathode compartments are electrically isolated to prevent electrolysis of water at higher voltages. The only ion transfer is through the lithium ion conductive glass-ceramic (LiC-GC) membrane, which selectively allows only lithium ions to flow. Therefore, the resulting lithium metal has a high purity. The inventor believes that the lithium metal has a purity of nearly 100 weight percent on a metals basis and at least greater than 99.99 weight percent on a metals basis.

The cathode support can be a linear slide in the z-axis (up and down). This can be a pneumatic cylinder with end stops to control travel (lowest cost), or a servo drive to precisely position (higher cost but more precise). With the cylinder retracted there is no electrolysis. When the cylinder extends it lowers the cathode into the electrolyte (while maintaining an electrolyte-filled space between the cathode and the lithium ion conductive glass-ceramic (LiC-GC) plate). Voltage is supplied to reduce lithium ions to lithium metal on the cathode. At any point the cathode can be withdrawn by retracting the cylinder, at which time electrolysis is stopped and the lithium metal is harvested from the cathode.

Figure 6:
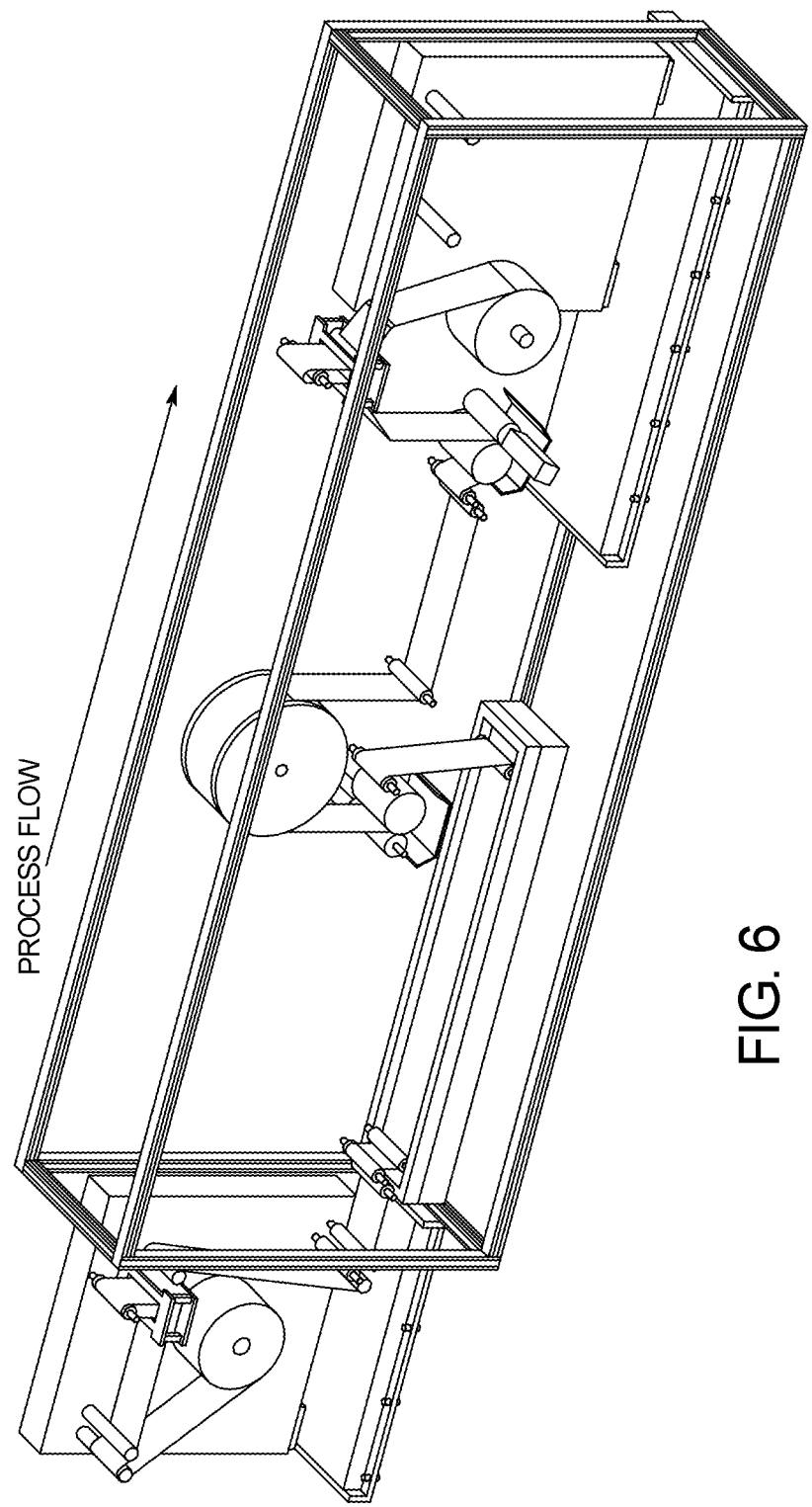
FIG. 6 shows a schematic view of a strip coating system according to an embodiment of the present disclosure.

In another embodiment, lithium metal produced from a lithium ion containing electrolyte is directly coated onto a strip of material using a strip coating system as shown in FIG. 6. Specifically, a high purity lithium metal can be coated onto a strip foil substrate such as aluminum, copper or nickel using this strip coating system. The strip foil substrate is connected to a plating power supply and acts as a cathode when submersed in a catholyte in a strip coating tank. A lithium ion containing electrolyte is separated from the catholyte by a lithium ion conductive glass-ceramic (LiC-GC) membrane. The lithium ion containing electrolyte flows through the bottom of the strip coating tank so that lithium ions are selectively conducted from the electrolyte through the catholyte and the lithium ion conductive glass-ceramic (LiC-GC) membrane and lithium metal is deposited on the strip foil substrate.

The catholyte of FIG. 6 may have the same composition as catholyte 10 described above in connection with FIG. 3. For example, the catholyte may be a simple lithium battery electrolyte such as a mixture of ethylene carbonate (EC), dimethyl carbonate (DMC) and an electrolyte salt such as lithium hexafluorophosphate (LiPF$_6$), a mixture of dimethyl carbonate and lithium hexafluorophosphate (DMC-LiPF$_6$), or a more complex lithium ion conducting barrier film.

The selective lithium ion lithium ion conductive glass-ceramic (LiC-GC) membrane is a lithium ion conductive glass-ceramic layer. Suitable materials for the glass-ceramic layer include the same materials for the lithium ion conductive glass-ceramic (LiC-GC) layer 30 of the embodiments of the lithium producing cell structure described above in connection with FIG. 1 or 3.

The lithium ion containing electrolyte is an electrolyte containing lithium ions and may have the same composition as electrolyte 18 of the embodiment described above in connection with FIG. 1 or the electrolyte 11 of the embodiment described above in connection with FIG. 3. For example, the lithium ion containing electrolyte may comprise a lithium salt such as lithium carbonate that is dissolved in hydrated acid such as sulfuric acid. A preferred electrolyte is a sulfuric acid electrolyte that contains lithium ions.

Figure 7:
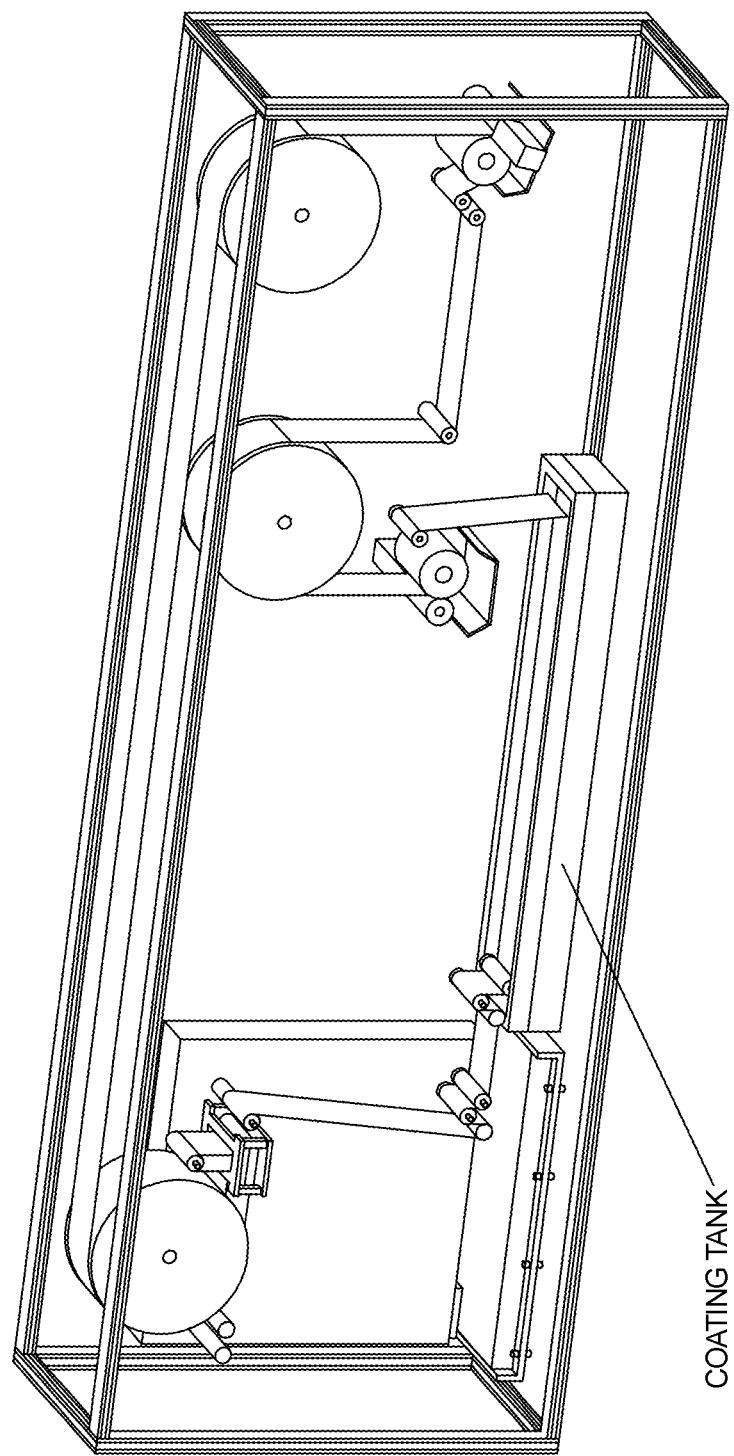
FIG. 7 shows a schematic view of a continuous strip coating system according to another embodiment of the present disclosure.

In another embodiment, lithium metal produced from a lithium ion containing electrolyte is directly coated onto a strip of material, and is then converted to a lithium compound using a continuous strip coating system as shown in FIG. 7. High purity lithium metal is coated onto a continuous strip material such as aluminum, copper, graphite coated copper, or nickel using this strip coating system. The continuous strip material is connected to a plating power supply and acts as a cathode when submersed in a catholyte in a strip coating tank. A lithium ion containing electrolyte is separated from the catholyte by a lithium ion conductive glass-ceramic (LiC-GC) membrane. The lithium ion containing electrolyte flows through the bottom of the strip coating tank so that lithium ions are selectively conducted from the electrolyte through the catholyte and the lithium ion conductive glass-ceramic (LiC-GC) membrane and lithium metal is deposited on the continuous strip material.

As shown in FIG. 7, the lithium-coated strip material may then be continuously fed into a system for producing a lithium compound such as lithium hydroxide. Specifically, the high purity lithium metal may be processed with deionized water to form lithium hydroxide and hydrogen according to the following reaction:

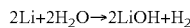

$$2Li+2H_2O \rightarrow 2LiOH+H_2$$

The hydrogen produced in this lithium hydroxide formation process may be vented off, burned off or stored. For example, the hydrogen may be burned off in air to form water, or simply vented to the atmosphere where it will combine with oxygen to form water vapor. Alternatively, the hydrogen may be captured in capsules or cartridges. The capsules or cartridges containing hydrogen may be used as rechargeable cartridges in a fuel cell battery for consumer electronics.

Figure 9:
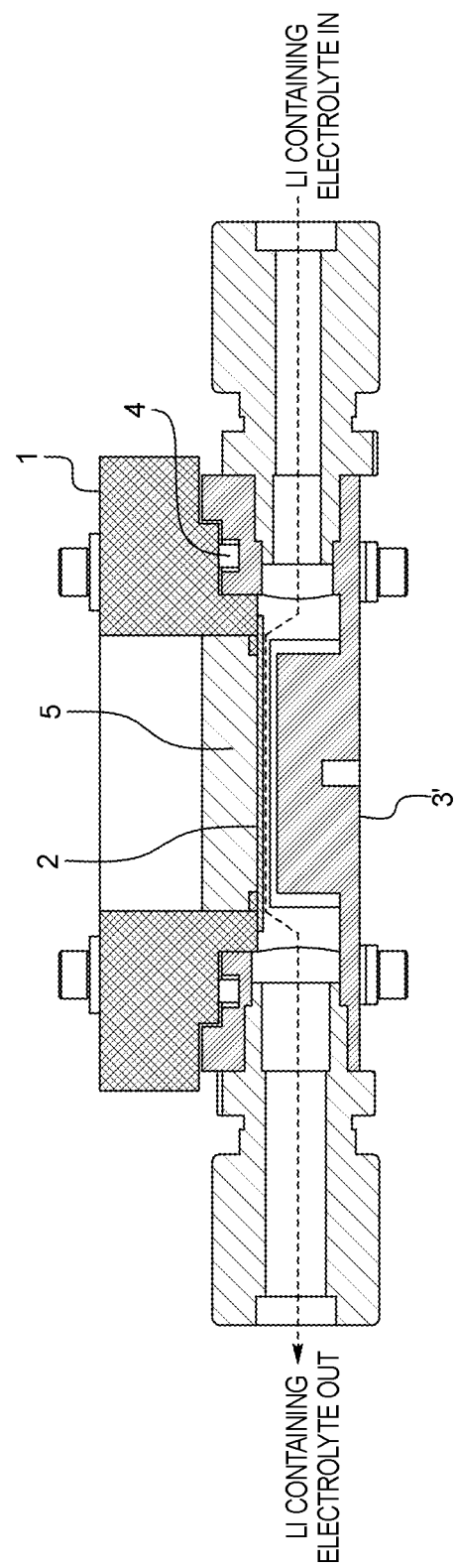
FIG. 9 is a section view of a lithium production cell according to another embodiment of the present disclosure.

A high purity lithium metal according to another embodiment may be produced using a cell as shown in FIG. 9. Suitable cell components for the cell of FIG. 9 include most of the same components disclosed for the previous embodiments of the lithium producing cell structure, specifically most of those cell components described in US20130004852. This embodiment eliminates the separate anode structure, and simplifies electrical connection to anode and sealing of an electrical connection. As seen in FIG. 9, the separate anode structure has been replaced by a conductive cell body 3', which now acts as the anode. The cell body 3' in this embodiment can be made of 904L stainless steel for sulfuric acid resistance. In a further embodiment, the cell body 3' can be made of 904L stainless steel with the inside flow surfaces plated with gold, platinum, ruthenium oxide, or other conductive material that has good conductive properties and is resistant to sulfuric acid. The lithium ion conductive glass-ceramic (LiC-GC) membrane 2 is bonded to non-conductive cell sleeve 1, providing a barrier between catholyte 5 and anolyte. The catholyte 5 in this embodiment is non-flowing for direct deposition onto a substrate. Square O-ring 4 seals the cell body 3' to cell sleeve 1.

Suitable feed to the cell of FIG. 9 includes the same materials disclosed for the previous embodiments of the lithium producing cell structure, specifically water-soluble lithium salts including but not limited to $Li_2CO_3$ (lithium carbonate) and LiCl. To improve solubility, as with the previous embodiments, the lithium salt is dissolved in hydrated acid such as sulfuric acid and used as electrolyte in the cell of FIG. 9.

The selective lithium ion conductive glass-ceramic (LiC-GC) membrane 2 is a lithium ion conductive glass-ceramic layer. Suitable materials for the glass-ceramic layer include the same materials for the lithium-ion conducting layer of the previous embodiments of the lithium producing cell structure. The electrolyte can be modified in the catholyte to produce a desired solid electrolyte interphase (SEI) layer, or none at all.

In the process using the cell of FIG. 9, anode and cathode compartments are electrically isolated to prevent electrolysis of water at higher voltages. The only ion transfer is through the lithium ion conductive glass-ceramic (LiC-GC) membrane, which selectively allows only lithium ions to flow. Therefore, the resulting lithium metal has a high purity.

Figure 10A:
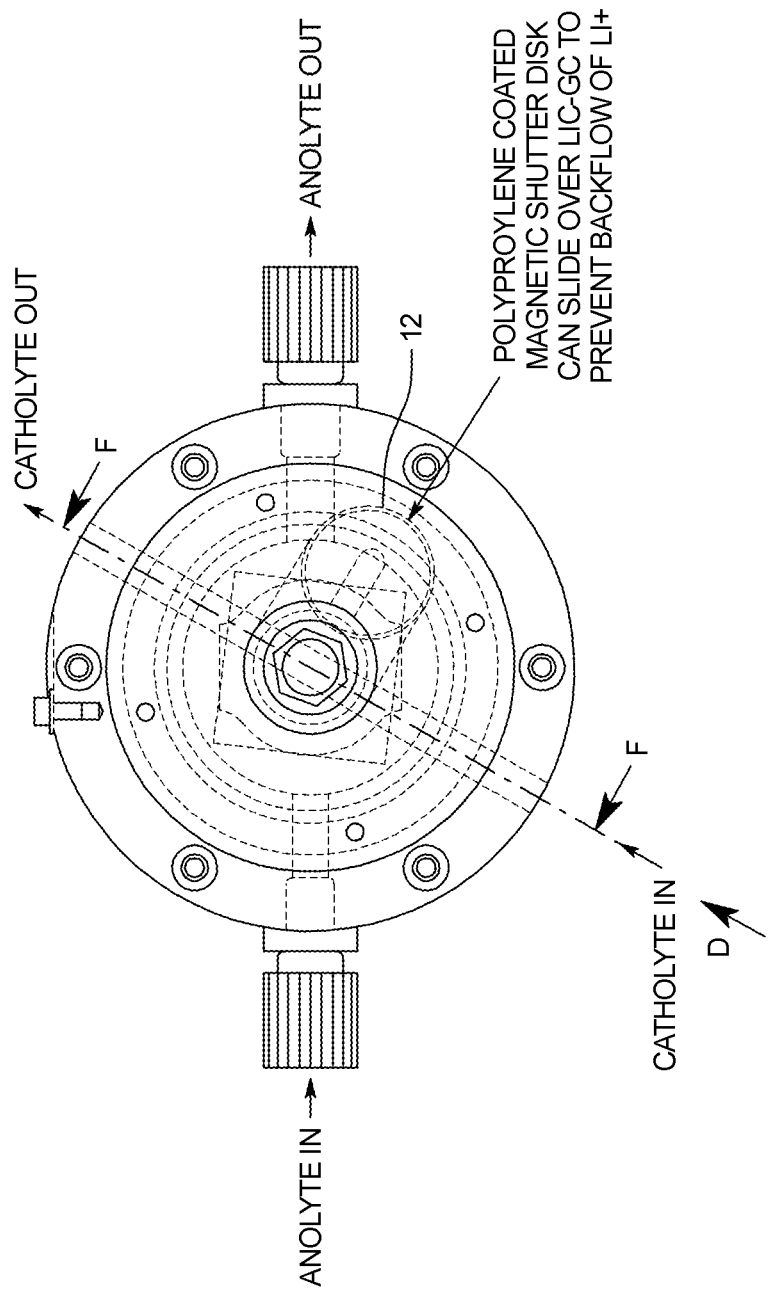
FIG. 10A is a schematic elevation view of a lithium producing cell according to another embodiment of the present disclosure.
Figure 10B:
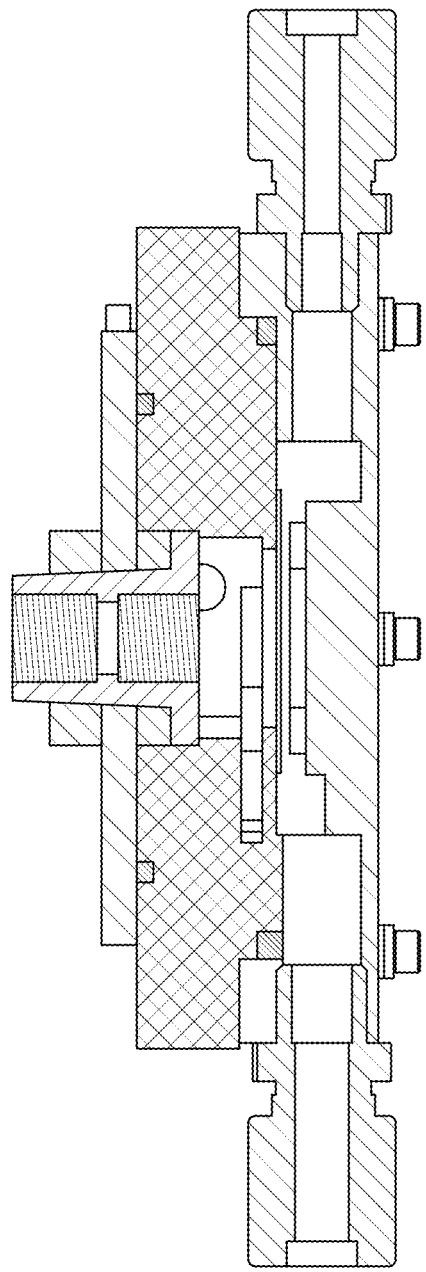
FIG. 10B is a section view of the lithium producing cell of FIG. 10A.

A high purity lithium metal according to another embodiment may be produced using a cell as shown in FIGS. 10A-10B. Suitable materials for the glass ceramic layer, cell components, feed, and electrolyte for the cell of FIGS. 10A-10B include the same materials for the glass ceramic layer, cell components, feed, and electrolyte disclosed for the cell of FIG. 9. This embodiment, like the cell of FIG. 9, eliminates the separate anode structure, and simplifies electrical connection to anode and sealing of an electrical connection. Unlike the cell of FIG. 9, FIGS. 10A-10B depict a cell with a closed top with catholyte flowing through the top half of the cell. The flowing catholyte is then processed to form LiOH.

The lithium metal produced according to certain embodiments has a high purity due to the selective conduction of lithium ions out of the lithium containing electrolyte. The inventor believes that the lithium metal produced according to certain embodiments has a purity of nearly 100 weight percent, and at least greater than 99.99 weight percent on a metals basis, or at least greater than 99.998 weight percent, due to the use of the selective lithium ion conducting layer. As further explained below, in an embodiment the inductively coupled plasma mass spectrometry (ICP-MS) analysis showed no presence of common impurities or base metals such as sodium, calcium, potassium, boron, magnesium, copper, iron, chlorine, aluminum, nitrogen, or silicon. The resulting high purity lithium metal may be used to make a lithium metal product and other products containing lithium metal.

Figure 8:
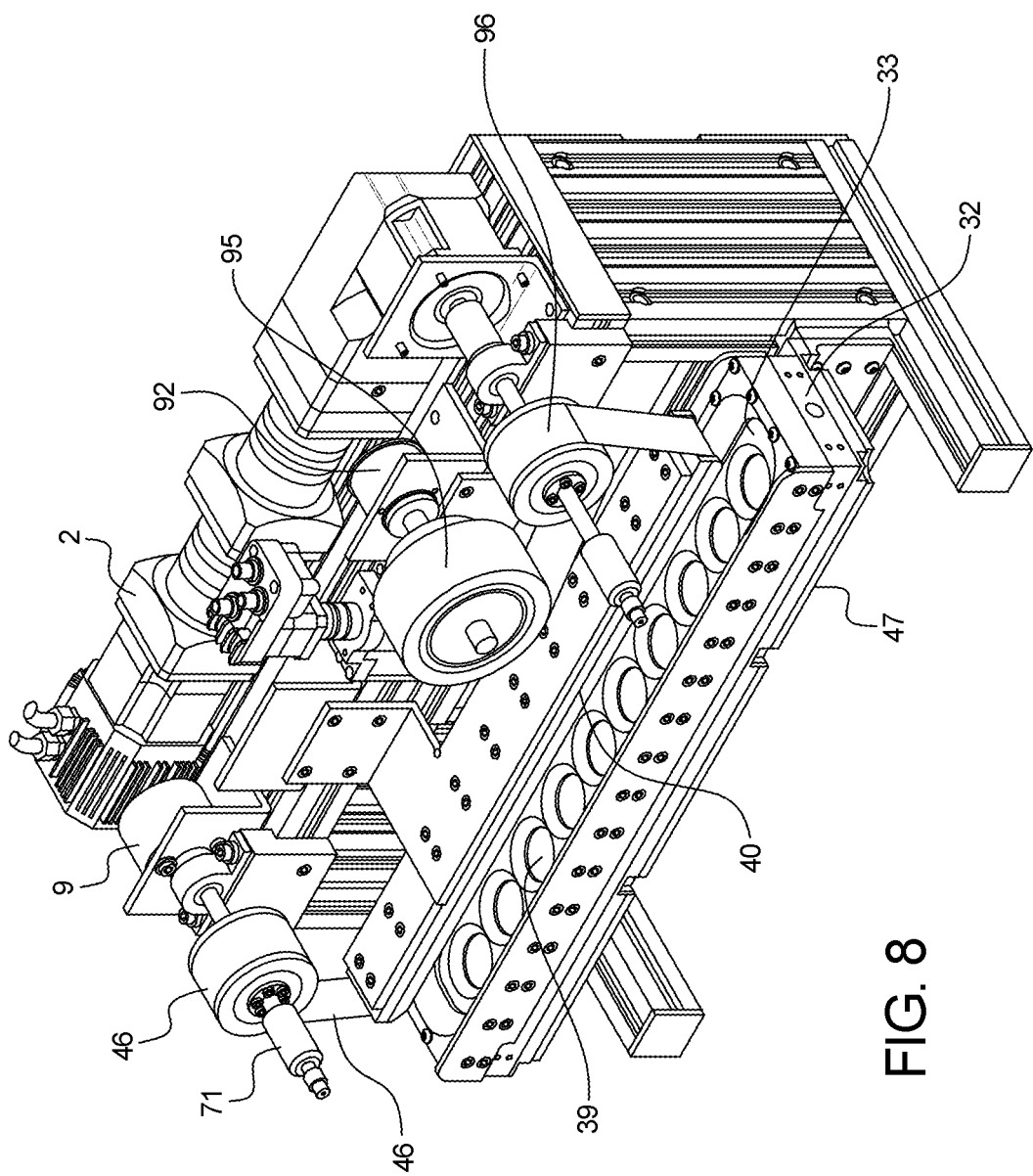
FIG. 8 shows a small-scale strip coating system according to another embodiment of the present disclosure.

In another embodiment, lithium metal produced from a lithium ion containing electrolyte is directly coated onto a strip of material and is then converted to a lithium compound using a continuous strip coating system as shown in FIG. 8. The roll of film to be coated is loaded onto payoff reel 46 with tension clutch 9. The film is thread under strip guide 40 and onto takeup reel 96. Polypropylene film 95 can also be threaded onto takeup reel 96 if desired to separate each layer of film. Tension clutch 92 controls the tension. Catholyte 33 is loaded into cavity above lithium ion conductive glass-ceramic (LiC-GC) plates 39. Platform 47 is raised to submerse submerse guide/film 40/46 in catholyte 33. Variable speed drive 2 controls film speed through the bath. DC voltage applied to the conductive housing of cell base 32 and the rotary contactors 71 at payoff and takeup reels. The energized strip is the cathode and cell base 32 is the anode. The film is processed through a bath at a controlled speed and voltage profile in order to coat film with high purity lithium metal at a desired thickness and morphology.

In an embodiment, the high purity lithium metal has a lithium purity of at least 99.99 weight percent on a metals basis when analyzed using an inductively coupled plasma mass spectrometry (ICP-MS) method. The remaining weight is representative of the resulting solid electrolyte interphase (SEI) layer produced from decomposition of catholyte. In an embodiment, 100% weight lithium can be produced upon entering the catholyte. This was verified by an inductively coupled plasma mass spectrometry (ICP-MS) method, where the high purity lithium metal is ionized with inductively coupled plasma and then subjected to mass spectrometry to separate and quantify the ions in the high purity lithium metal. In the inductively coupled plasma mass spectrometry (ICP-MS) method, the lithium metal may be placed in a <5% nitric acid solution that is free of particulates >0.45 μm in size and contains <2% organic materials. The total dissolved solids ("TDS") in the solution must be below 0.1% when diluted for inductively coupled plasma mass spectrometry (ICP-MS) determination. The inductively coupled plasma mass spectrometry (ICP-MS) analysis may be performed using a suitable inductively coupled plasma mass spectrometry (ICP-MS) instrument.

An embodiment of the high purity lithium metal of the present disclosure analyzed by the inductively coupled plasma mass spectrometry (ICP-MS) method contains, in parts per million by weight, less than 0.6 silver (Ag), less than 2 aluminum (Al), less than 0.2 arsenic (As), less than 0.1 gold (Au), less than 0.4 boron (B), less than 0.4 barium (Ba), less than 0.5 beryllium (Be), less than 0.1 bismuth (Bi), less than 4 calcium (Ca), less than 0.5 cadmium (Cd), less than 0.4 cerium (Ce), less than 0.4 cobalt (Co), less than 0.4 chromium (Cr), less than 0.4 cesium (Cs), less than 0.4 copper (Cu), less than 0.4 dysprosium (Dy), less than 0.4 erbium (Er), less than 0.5 europium (Eu), less than 0.7 iron (Fe), less than 0.4 gallium (Ga), less than 0.4 gadolinium (Gd), less than 0.3 germanium (Ge), less than 0.2 hafnium (Hf), less than 0.3 mercury (Hg), less than 0.3 holmium (Ho), less than 0.5 indium (In), less than 0.2 iridium (Ir), less than 0.5 potassium (K), less than 0.4 lanthanum (La), less than 0.1 lutetium (Lu), less than 5 magnesium (Mg), less than 0.3 manganese (Mn), less than 0.4 molybdenum (Mo), less than 0.3 niobium (Nb), less than 0.4 neodymium (Nd), less than 0.9 nickel (Ni), less than 0.4 osmium (Os), less than 10 phosphorus (P), less than 0.1 lead (Pb), less than 0.5 palladium (Pd), less than 0.4 praseodymium (Pr), less than 0.2 platinum (Pt), less than 0.4 rubidium (Rb), less than 0.1 rhenium (Re), less than 0.3 rhodium (Rh), less than 0.4 ruthenium (Ru), less than 13 sodium (Na), less than 19 sulfur (S), less than 0.3 antimony (Sb), less than 0.5 scandium (Sc), less than 1 selenium (Se), less than 69 silicon (Si), less than 0.5 samarium (Sm), less than 0.7 tin (Sn), less than 0.5 strontium (Sr), less than 0.1 tantalum (Ta), less than 0.3 terbium (Tb), less than 0.4 tellurium (Te), less than 0.1 thorium (Th), less than 0.4 titanium (Ti), less than 0.1 thallium (Tl), less than 0.2 thulium (Tm), less than 0.1 uranium (U), less than 0.5 vanadium (V), less than 0.2 tungsten (W), less than 0.4 yttrium (Y), less than 0.2 ytterbium (Yb), less than 1 zinc (Zn), and less than 0.3 zirconium (Zr). Thus, the total impurities in the lithium metal are less than 0.002 weight percent.

In an embodiment, the high purity lithium metal has a lithium purity of at least 99.998 weight percent on a metals basis. In an embodiment, the high purity lithium metal has no impurities above the minimum detectable limit of the inductively coupled plasma mass spectrometry method (ICP-MS) method. In an embodiment, the high purity lithium metal has no impurities.

Figure 11A:
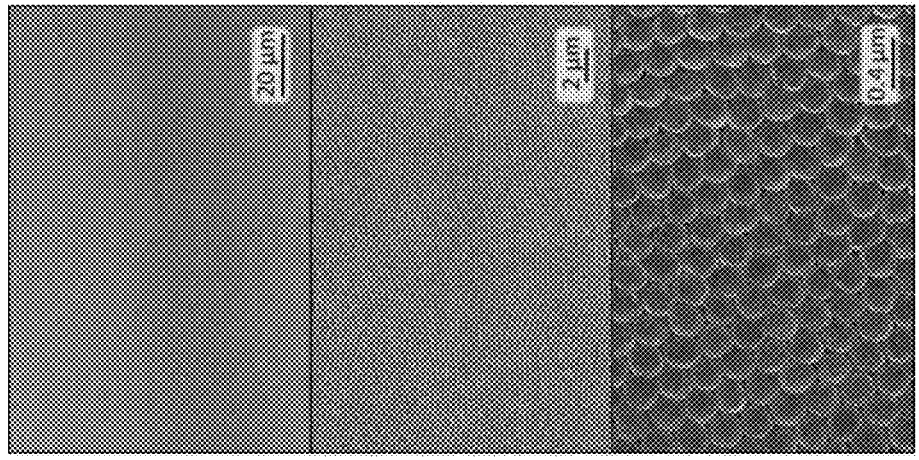
FIG. 11A shows a series of micrographs of a lithium film according to the present disclosure (99.998% metals basis; 100 μm thickness) on Cu as compared to the prior art lithium foil.
Figure 11A:
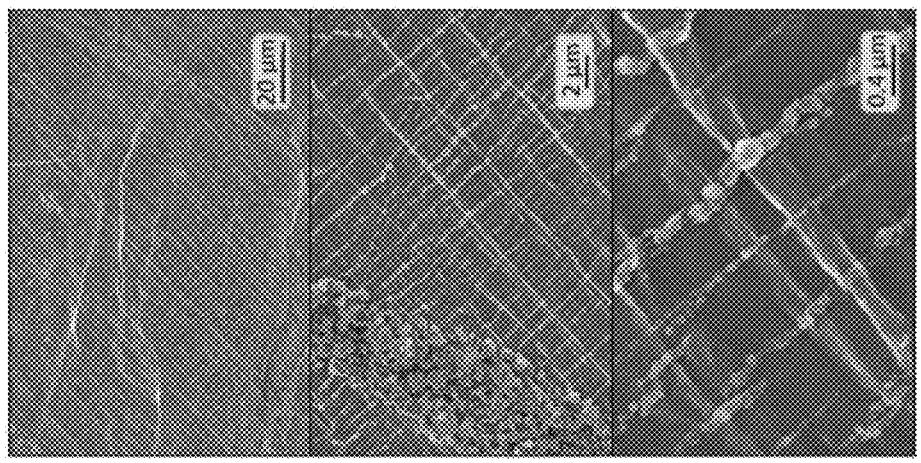
Figure 11B:
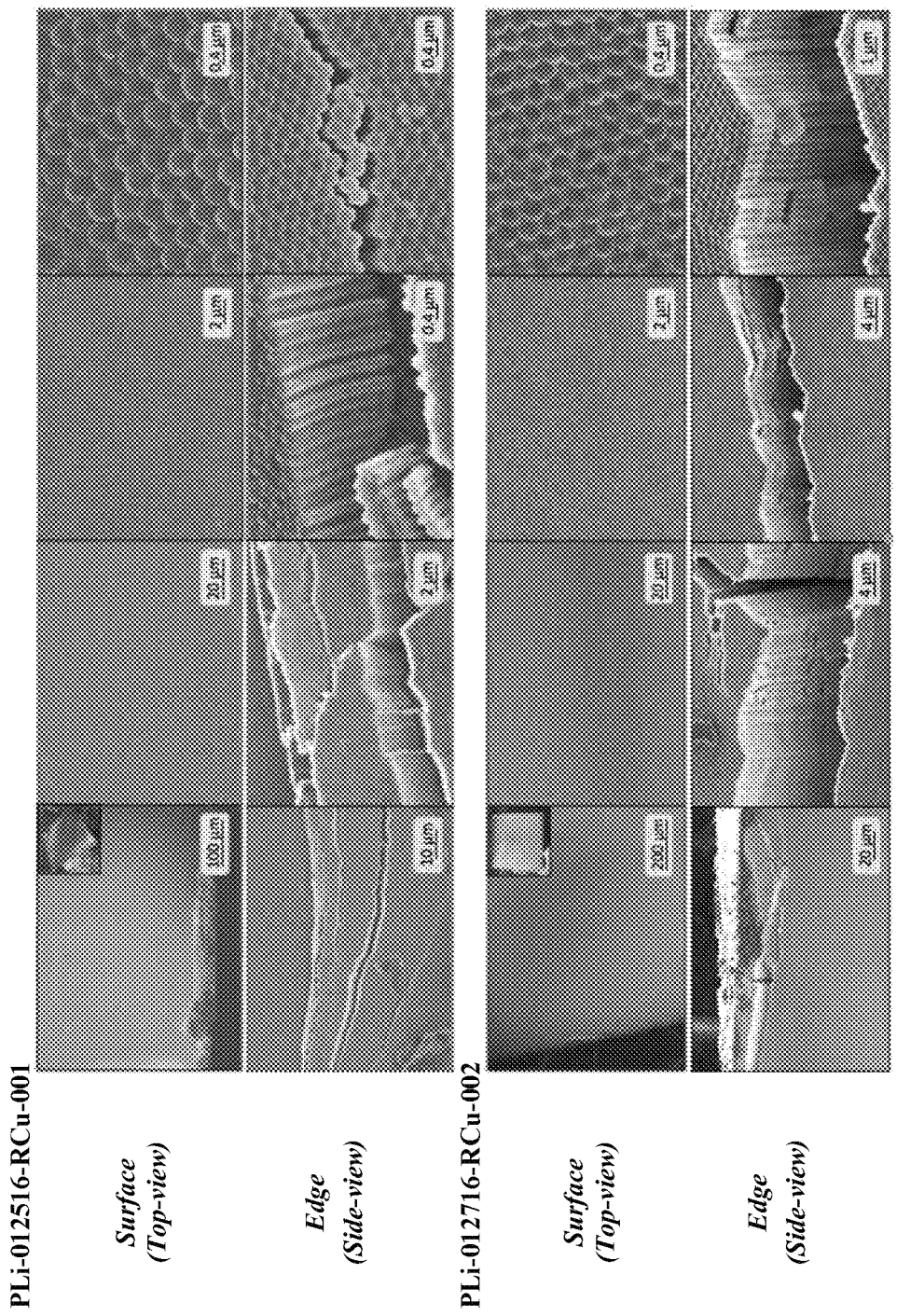
FIG. 11B shows a series of micrographs of surface views and edge views of a lithium film according to the present disclosure (99.998% metals basis; 100 μm thickness) on Cu.

Depending on the parameters, such as applied current and voltage, the lithium obtained according to an embodiment of the present disclosure can assume a nanorod morphology. As opposed to the lithium foil obtained by conventional processes, the self aligned nanorods provide a higher surface area for lower impedance and increased rate capability. The nanorod morphology also has the benefits of a highly desirable diffusion coefficient and flexible deposition. Moreover, the lithium is free of a variety of non-conductive contaminants and impurities which can cause undesirable side reactions. The micrographs of FIGS. 11A-11B illustrate the difference between a lithium foil obtained by a prior art process and a lithium nanorod obtained via the current disclosure. On the right side of FIG. 11A, the three different micrographs show a lithium film according to the present disclosure (99.998% metals basis; 100 μm thickness) on copper having an unexpected self aligned nano-rod morphology (300 nm diameter×100 μm length) of the electrodeposited lithium metal. Notably, this nano-rod configuration has a smoother surface that is dendrite free. In contrast, the three different micrographs of the prior art lithium foil (99.9% metals basis; 750 μm thickness) show a surface with dendrite arms, as well as surface defects and cracks which serve as nucleation sites for further dendrite growth.

Figure 12:
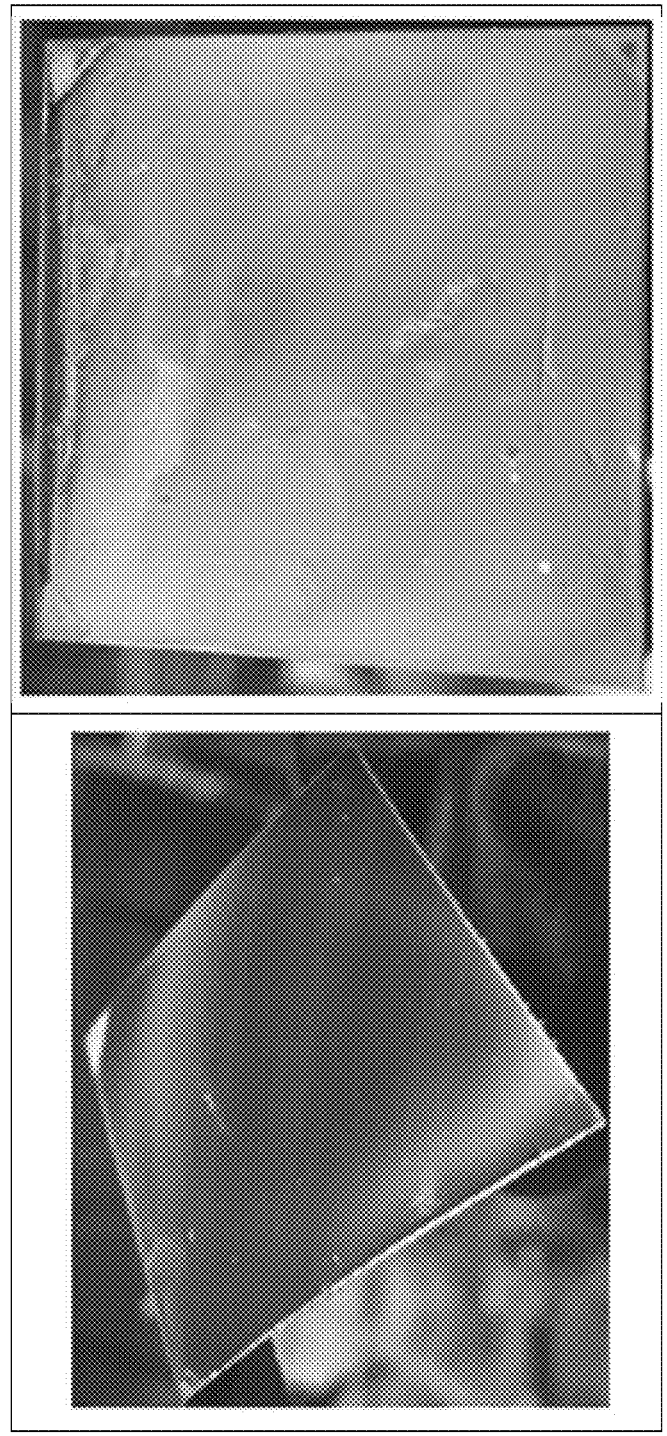
FIG. 12 shows two optical micrographs of lithium films according to the present disclosure on copper samples.

FIG. 12 shows two optical micrographs of lithium samples according to the present disclosure on copper. The weight for the lithium metal film is 50 mg. The dimensions for the copper foil substrate are 3 cm×3 cm (area)×125 μm thickness. Regarding the sample on the right side of FIG. 12, a bluish color was observed for the film, which is a positive indication of high purity and smoothness. The blue appearance might be due to a structural coloration effect, whereby the fine microscopic surface produces a structural color by interference among light waves scattered by two or surfaces of the thin film.

In an embodiment, the present disclosure provides a process for separating Lithium-6 and Lithium-7 isotopes from a lithium metal, the process comprising: providing an electrolytic cell comprising an organic aqueous solution, a nonaqueous electrolyte and a selective lithium ion conducting membrane, and causing the Lithium-6 and Lithium-7 isotopes in the lithium metal to pass through the membrane at different velocities, and capturing at least one of the Lithium-6 and Lithium-7 isotopes. This process can, for example, be run at least two times using a specific electrolyte. Suitable electrolytes include crown ethers such as 18-Crown-6 $[C_2H_4O]_6$ and 2,2,2-cryptate; both form very stable complexes in both gas and solution phase, and have a high affinity for cations. Other suitable solvents include dimethylformamide (DMF) $(CH_3)_2NC(O)H$, and dimethyl sulfoxide (DMSO) $(CH_3)_2SO$, both polar aprotic solvents, and dimethylacetamide (DMA) $CH_3C(O)N(CH_3)_2$. Polyethelene glycol (PEG) mixed with ammonium sulfate $(NH_4)_2SO_4$ and solvents producing different solvation states for lithium ions in two aqueous phases produce a usable separation factor. Macrolyclic polyethers offset solvation of the cation by water molecules in the PEG rich phase.

For separation of Li-6 and Li-7 isotopes, an aqueous electrolyte could be used on both sides of the membrane until the final metal deposition stage. Multiple aqueous-aqueous stages could be used to enrich with the final deposition stage using a non-aqueous electrolyte. For the aqueous-aqueous stages, the LiC-GC membrane could be used, or another membrane such as a polyethylene composite or garnet, which allow for proton transfer, could be used. The final deposition stage which uses a non-aqueous electrolyte would require a membrane with extremely low moisture permeability such as the LiC-GC membrane.

In an embodiment, the present disclosure provides a process to obtain an enriched Lithium-6 isotope and/or an enriched Lithium-7 isotope from Lithium metal. The enrichment process was performed using the cell of FIG. 3. Samples of $Li_2CO_3$ (feedstock) and the resulting two samples of Lithium metal products were analyzed for isotopic ratio. In one example, a decrease in lithium-7 fraction by approximately 1.04 and an increase in lithium-6 fraction by approximately 1.17% was observed.

The high purity lithium-7 and lithium-6 may be used for applications in nuclear power. For example, lithium-7 hydroxide is used as an additive in pressurized water reactor cooling systems as a pH stabilizer, and lithium-6 is a source of tritium for nuclear fusion.

The high purity lithium may advantageously be used in the following products: a lithium metal electrode, preferably a lithium metal anode; and a battery including the lithium metal electrode, preferably a lithium primary battery or a rechargeable battery having a lithium metal anode. By including the high purity lithium in a lithium metal electrode of a battery, the electrode should not induce the formation of dendrites when undergoing charge and discharge cycles (due to the presence of fewer impurities), and, thus, a battery containing the high purity lithium metal electrode advantageously achieves a high energy density while simultaneously achieving good safety due to the reduction of short-circuiting caused by dendrite formation.

In another embodiment, the present disclosure provides an improved lithium battery containing the high purity lithium. The improved lithium battery may include a lithium metal electrode containing the high purity lithium. The lithium metal electrode containing the high purity lithium may preferably be used as an anode in the improved lithium battery. The improved lithium battery advantageously does not contribute to dendrite growth during cycling than batteries having a lithium metal electrode with a lower lithium purity (i.e., 99.9% or less). Therefore, the improved lithium metal battery may be a primary battery or a rechargeable battery that undergoes repeated charge and discharge cycles without significant dendrite formation. The improved lithium metal battery may use an electrode produced with a protective layer via atomic layer deposition (ALD), and a specific solid electrolyte interphase (SEI) controlled by the catholyte. The improved lithium metal battery advantageously achieves a high energy density, cycle life, rate capability and low impedance and can withstand pulse without compromising battery safety due to short-circuiting caused by dendrite formation.

Alternatively, the improved lithium battery may include an electrode containing a lithium compound formed using the high purity lithium. The lithium compound may be any known lithium compound that is used for an electrode in a lithium battery, including but not limited to: a lithium oxide containing cobalt, nickel, aluminum, manganese or mixtures thereof, such as lithium cobalt oxide ($LiCoO_2$) or lithium nickelate ($LiNiO_2$); a lithium phosphate such as lithium cobalt phosphate ($LiCoPO_4$), lithium iron phosphate ($LiFePO_4$) or lithium manganese phosphate ($LiMnPO_4$); a lithium chalcogenide such as $LiTiS_2$ or $LiVSe_2$; a lithium layered oxide; and a lithium alloy. When the high purity lithium metal is used to form the lithium compound in the electrode, the overall lithium compound has a high purity and does not contain the impurities typically associated with lithium metal, the concentration of the active material is increased, and, thus, battery characteristics such as cycle life, charge-discharge rate capability, and impedance can be improved.

The improved lithium battery may advantageously be used in products including but not limited to portable consumer electronic devices, military batteries, micro batteries, lithium-ion batteries, space (wearable and craft) and satellite batteries, drone batteries, flexible batteries, sensor batteries that can withstand a pulse, medical devices, toys, clocks, cameras and oceanographic equipment, or devices using "Battery on Board", a battery meant to exceed the life of the product. For example, the improved lithium battery may be used in a camera such as a digital camera. Digital cameras and drones are notorious for draining battery life due to high energy consumption by the LCD screen (which contains lithium) and the motors that move the mechanical components of the camera. Therefore, it is desirable to have a digital camera that has a higher energy density and longer battery life so that the camera does not shut down at undesirable times when trying to take a picture. Conventional lithium metal primary batteries have a high energy density and can therefore be made more compact and have a longer battery life as compared with lithium ion batteries. However, such primary batteries suffer dendrite formation due to the impurities in the lithium metal anode, and do not handle electrochemical pulses well, and use lithium of significantly less purity. By using a lithium metal battery containing an anode having the high purity lithium as described above, the active material (lithium metal) is increased, resulting in substantially longer life, capacity, lower impedance and dendrite formation can be reduced or eliminated, thereby giving the digital camera a longer battery life and higher safety as compared with conventional lithium metal batteries. Alternatively, by using a lithium battery including an electrode containing a lithium compound formed using the high purity lithium, the impurities in the electrode material can be reduced, thereby improving the cycle life so that the digital camera has a longer battery life.

The improved lithium battery may also be used in a camcorder. A longer battery life is desirable for camcorders so that they can record events that have a longer duration or a series of shorter events without needing to frequently replace or recharge the battery. A battery with a high energy density is also desirable so that the camcorder can be made more compact and, thus, easier to carry and hold when recording. By using a lithium metal battery containing an anode having the high purity lithium as described above, dendrite formation can be reduced while simultaneously achieving a high energy density, thereby giving the camcorder a longer battery life and higher safety without unnecessary bulkiness. Alternatively, by using a lithium battery including an electrode containing a lithium compound formed using the high purity lithium, the impurities in the electrode material can be reduced, thereby giving the camcorder a longer battery life.

The improved lithium battery may also be used in a computer such as a laptop computer or a tablet computer. The most common type of battery used in portable computers such as a laptop or tablet is a lithium ion rechargeable battery. By using a lithium battery, for example a lithium ion battery, including an electrode containing a lithium compound formed using the high purity lithium as described above, the computer can have a longer cycle life and, thus, the computer will not need to be recharged as often as conventional lithium ion batteries. As a result, the computer can be used for longer periods of time without needing to be plugged in or recharged. By using a lithium metal battery having a lithium metal anode containing the high purity lithium as described above, the battery life and energy density of the computer battery can be further improved as compared with conventional lithium ion batteries, without compromising the safety of the computer. Therefore, the computer can be made more compact and have a longer battery life. Furthermore, the battery will be less prone to "swelling" and, thus, the computer will be less prone to heating up during use.

The improved lithium battery may also be used in a cellular phone such as a smart phone. Cellular phones need compact batteries so that the cellular phone may be made smaller and, thus, more easily portable. However, cellular phones such as smart phones also use a lot of power, since many such phones include LCD screens (which contain lithium), cameras and video recorders. Therefore, it is desirable to provide a cellular phone that can be made compact but also has a high energy density. By using a lithium metal battery having a lithium metal anode containing the high purity lithium as described above, the high energy density of lithium metal can be utilized to provide more power with a smaller battery, as well as a longer battery life as compared with conventional lithium ion batteries used in cellular phones. Even if the high purity lithium metal is used to form a lithium compound in a lithium ion battery, a cellular phone containing such a lithium ion battery will have a longer cycle life than conventional lithium ion batteries due to the improved purity of the lithium compound in the electrode and the lack of impurities associated with lithium produced by conventional processes.

The improved lithium battery may also be used in a personal digital assistant. Like cellular phones, personal digital assistants ("PDAs") are portable but require high power to store a significant amount of data and, thus, it is desirable to make personal digital assistants as compact as possible while also achieving a high energy density. By using a lithium metal battery having a lithium metal anode containing the high purity lithium as described above, the personal digital assistant can make use of the high energy density of lithium metal to provide a more compact design while also having a high amount of power. In addition, because the amount of impurities in the lithium metal anode is reduced, dendrite formation is inhibited and, thus, the personal digital assistant has both high safety and high energy density. Alternatively, if the personal digital assistant includes a lithium battery, for example a lithium ion battery, using a lithium compound electrode material containing the high purity lithium as described above, the personal digital assistant can have a longer cycle life and, thus, will not need to be recharged as often as a personal digital assistant using a conventional lithium ion battery.

The improved lithium battery may also be used in small devices such as a clock, a watch, a remote car lock, a remote control for an audio or audiovisual device such as a television, a remote control for smart home devices, sensors, drones, a DVD player, a compact disc player, or a media streamer. Due to the small size of these devices, a very compact battery that provides a high energy density is required. Therefore, these devices may desirably include a lithium metal battery using an anode containing the high purity lithium as described above. By using such a lithium metal battery, the small remote control devices can make use of the high energy density of lithium metal to provide a more compact design while avoiding the problems associated with dendrite formation in most lithium metal batteries. Alternatively, if the devices include a lithium ion battery containing the high purity lithium metal (e.g., the high purity lithium metal is used to form a lithium compound used in the electrode), the remote control devices will have a longer cycle life than devices using a conventional lithium ion battery.

The improved lithium battery may also be used in an electric vehicle. Lithium ion batteries are desirable for use in electric vehicles due to their small size and low weight, as well as their charge efficiency. However, an electric vehicle containing a lithium ion battery using the high purity lithium metal (e.g., the high purity lithium metal is used to form a lithium compound used in the electrode) will have a higher energy density than conventional lithium ion batteries, and, thus, the electric vehicle will be able to provide more power without increasing the battery size. The electric vehicle can be further improved by using a lithium metal battery containing the high purity lithium metal as an anode, cathode or electrolyte material. Because the lithium metal anode has fewer impurities, dendrite formation will be inhibited and, thus, the electric vehicle will be able to utilize the high energy density of lithium metal without suffering the safety issues associated with dendrite formation. As a result, the electric vehicle can provide more power and a longer battery life without increasing the battery size. In an embodiment, the electric vehicle may also be less prone to fires due to the improved lithium metal purity.

The improved lithium battery may also be used in implantable medical devices such as a cardiac pacemaker, a drug delivery system such as an insulin pump, a neurostimulator, implantable sleep apnea device, a deep brain neurostimulator, gastric stimulators, a cardiac defibrillator, a ventricular assist device, a hearing assist device such as a cochlear implant, a contact lens that measures glucose of tears and wirelessly transmits data to a medical doctor, a cardiac resynchronization device, a bone growth generator, and an artificial heart. Because implantable medical devices are typically essential to a patient's health, it is undesirable to leave the responsibility for charging the battery to the patient. Implantable medical devices also need a long battery life so that they do not have to be replaced often with invasive medical procedures. Therefore, these medical devices commonly use lithium primary batteries having a lithium metal anode. By using a lithium metal battery including an anode formed of the high purity lithium metal as described above, dendrite formation can be reduced and, thus, the high energy density and long battery life associated with lithium metal anodes can be utilized to provide an implantable device having a long battery life without the short-circuiting and safety problems associated with conventional lithium primary batteries. The improved thin film lithium solid state battery may also be used in external medical devices.

The improved lithium battery may also be used in oceanographic equipment. Oceanographers often work in remote locations that are difficult and costly to travel to and, thus, the oceanographers need battery packs having a longer life so that the oceanographic equipment does not need to be serviced as often. By using a lithium metal battery having an anode containing the high purity lithium as described above, the oceanographic equipment can have a longer battery life without the associated safety/dendrite formation problems associated with conventional lithium primary batteries. The improved lithium battery with a specific solid electrolyte interphase (SEI) layer will improve the safety and performance of batteries used in oceanographic applications, such as water drones and other devices.

The improved lithium battery may be a lithium primary battery, a rechargeable lithium metal battery, a rechargeable lithium-ion battery, a thin film lithium-ion battery, a micro battery, a flexible thin film battery, a lithium-ion polymer battery, a lithium iron phosphate battery, a lithium sulfur battery, a lithium-air or metal-air battery, solid state rechargeable battery, or a nanowire battery. When the improved lithium battery includes a lithium metal electrode, anode or electrolyte containing the high purity lithium, the battery advantageously achieves a high energy density without compromising battery safety due to short-circuiting caused by dendrite formation. When the improved lithium battery includes an electrode containing a lithium compound formed using the high purity lithium, battery characteristics such as cycle life and charge-discharge rate capability can be improved due to the enhanced overall purity of the lithium compound.

The high purity lithium may advantageously be used as a flux for welding or soldering applications to absorb impurities and thereby promote the fusing of metals. Because the lithium metal has a higher purity than lithium metal currently on the market, the flux is able to absorb more impurities and thus better promote the fusing of metals by preventing oxidation of the metals to be fused.

The high purity lithium may also advantageously be used in alloys or compounds containing lithium. For example, lithium salts containing the high purity lithium, such as lithium carbonate, lithium citrate and lithium orotate, may be used in the pharmaceutical industry as mood stabilizers to treat psychiatric disorders such as depression and bipolar disorder. Purity is especially important in medicinal products due to their use by humans or other animals. By providing the medicinal compound containing the high purity lithium metal as described above, the overall purity of the compound can be improved as compared with lithium compounds prepared using lithium metal produced by conventional processes. As another lithium alloy example, Alcoa uses a lithium aluminum alloy in the body of airplanes to make them lighter. Using higher purity lithium decreases impurities in the alloy, improving the performance and reducing interstitial defects. Improved alloy could be used in the frame of an electric vehicle (EV) to lighten the weight resulting in longer lasting driving range.

The high purity lithium may also be used in a lithium soap such as lithium stearate; a grease containing a lithium soap; lithium oxide; ovenware containing a lithium oxide; lithium fluoride; an optical material containing lithium fluoride; an optical material containing a lithium compound; an organolithium compound; a polymer containing an organolithium compound; lithium hydride; and an alloy containing lithium metal. Because the lithium metal has a higher purity than lithium metal currently on the market, the lithium compounds or alloys produced using the high purity lithium desirably have a lower overall impurity level.

In an embodiment, the electrolytic cell can be a flow cell, a cell with bulk catholyte, or a stand-alone flow battery. The anolyte side of the cell operates in the same way as previous embodiments. A sulfuric acid solution which dissociates lithium carbonate placing lithium ions into solution and venting off $CO_2$ is the preferred anolyte system, but the alternatives previously proposed are also acceptable. The catholyte side of the cell is a flow system or bulk fluid system which contains a 100% volatile electrolyte. Alternatively, LiOH can be the electrolyte so that the only non-volatile portion is the same LiOH produced. For the purpose of manufacturing lithium hydroxide monohydrate, a weak electrolyte of such as ammonium hydroxide, $NH_3(aq)$ (ammonia in water), or other suitable electrolytes, such as LiOH solution, could be used. The system could be operated at atmospheric pressure below the boiling point of the $NH_3(aq)$ electrolyte (27 degrees Celsius), or the sealed system could have pressure equalized and raised slightly on each side of the system (minimized pressure gradient across the lithium ion conductive glass-ceramic (LiC-GC) membrane) to raise the boiling point of the $NH_3(aq)$ solution. Other 100% volatile catholytes could be used. A 100% volatile catholyte with higher conductivity may be desirable.

If lithium hydroxide (LiOH) is used as the electrolyte, the concentration of LiOH increases during processing as lithium is processed through the membrane. As the concentration of LiOH increases and the solution pH increases, portions of the LiOH electrolyte can be periodically bled off and dehydrated, being replaced by deionized water to lower the pH of the solution back down to the desired operating range; a continuous control, maintaining a specific concentration in the circulating catholyte, could also be used. In such cases, operating temperature can be raised (though remaining below the boiling point of the LiOH electrolyte) to increase conductivity of the LiC-GC membrane.

The conductivity of lithium ion conductive glass-ceramic (LiC-GC) plate is approximately $3 \times 10^{-4}$ S/cm or 0.3 mS/cm at room temperature. Conductivity of a 5-10% $NH_3(aq)$ solution is approximately 1115 mS/cm at room temperature. Voltage applied to the cell results in migration of lithium ions across the membrane into the catholyte. The exact voltage versus $Li^+$ ion flow rates through the lithium ion conductive glass-ceramic (LiC-GC) plate need to be determined. If voltage is held below the potential required to convert lithium ions into lithium metal then the lithium ions would remain in solution in the catholyte. While not wishing to be bound by theory, it is believed that if voltage is raised until the current flows (which indicates Li-M production at the cathode), and then lowered until current is zero, $Li^+$ is still passing through the lithium ion conductive glass-ceramic (LiC-GC) plate. If the voltage required to provide an acceptable lithium transfer rate across the membrane results in plating of lithium metal at the cathode then the lithium metal can be dissolved back into the catholyte by using a shutter over the lithium ion conductive glass-ceramic (LiC-GC) membrane. With the non-conductive (such as polypropylene) in place then the lithium metal should react with and dissolve into the catholyte solution.

The catholyte solution could then be converted into lithium hydroxide monohydrate by either bulk processing of the bulk catholyte, or a continuous distillation process for a flowing catholyte. For bulk processing, the bulk catholyte is transferred to a vacuum chamber where the catholyte is heated to drive off the volatile electrolyte, leaving behind pure lithium metal or lithium hydroxide (when water is the final component to evaporate off). When $NH_3(aq)$ is used as the catholyte, the $NH_3$ should evaporate off first and can be reclaimed in a condenser. The water is then evaporated off and reclaimed also. The result is lithium hydroxide (anhydrous) or lithium hydroxide monohydrate depending on the level of drying.

By way of example and not limitation, the following examples are illustrative of various methods of producing the high purity lithium metal of the present disclosure. The processes below are provided for exemplification only, and they can be modified by the skilled artisan to the necessary extent, depending on the special features that are desired.

EXAMPLES

Example 1

Figure 4:
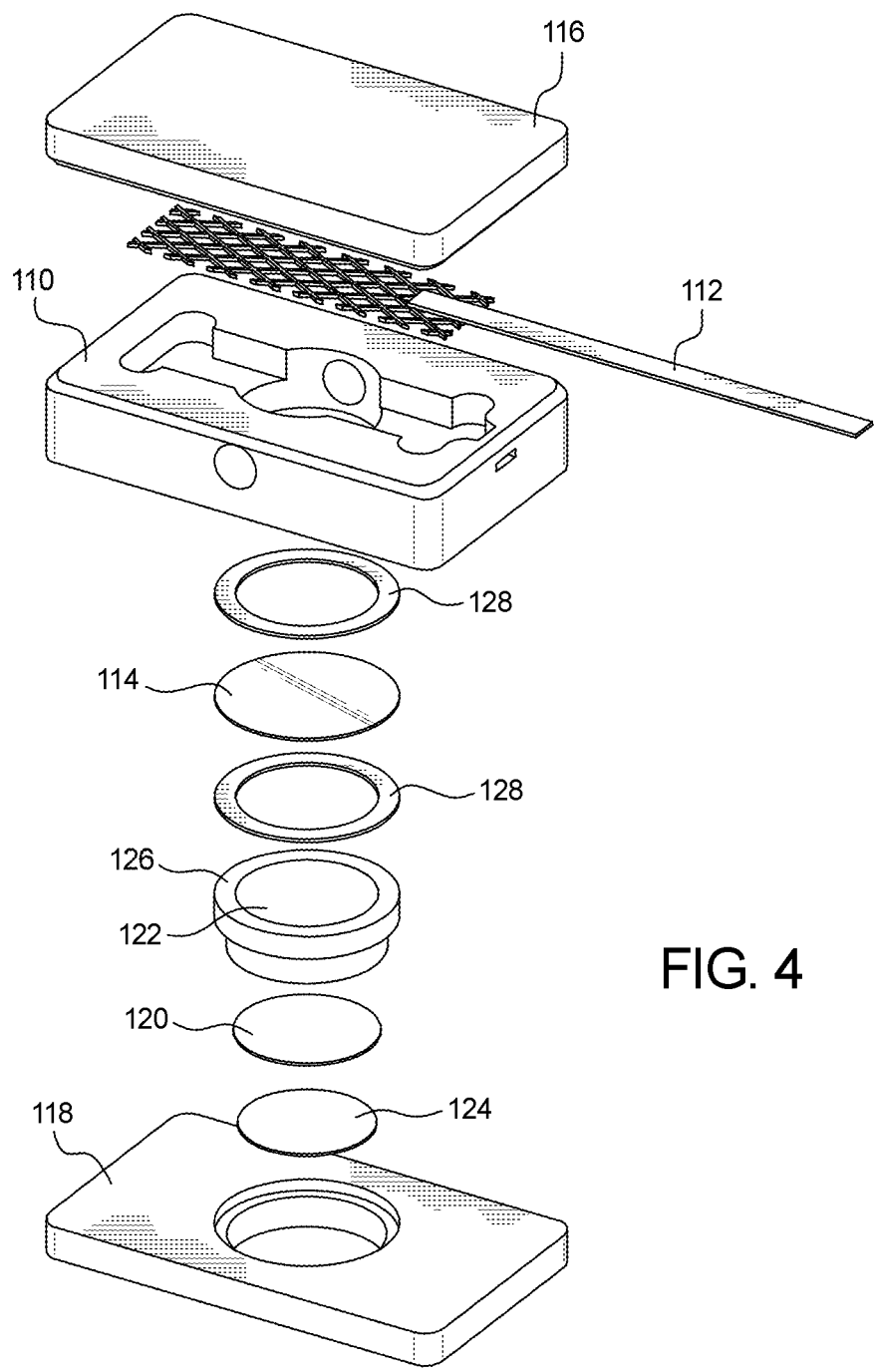
FIG. 4 shows a schematic exploded view of a lithium producing cell of Example 1.
Figure 5:
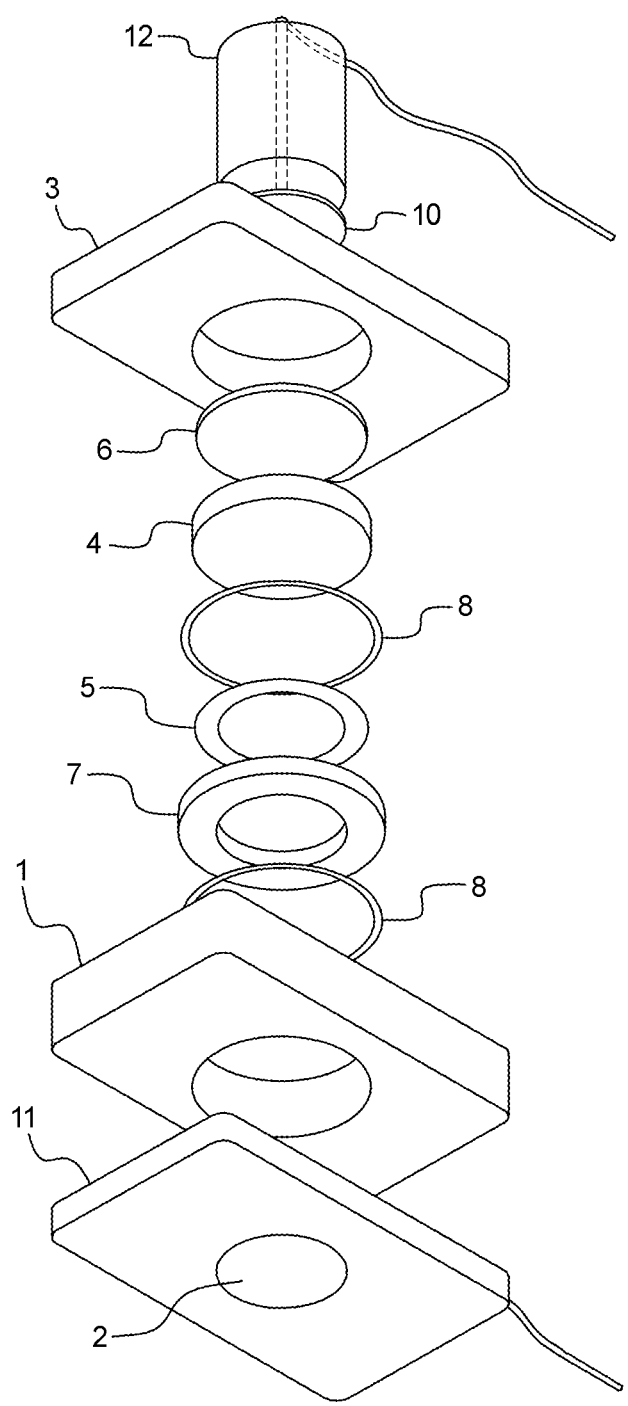
FIG. 5 shows schematic views of insertion/retraction module-adapted cells.

The cell used for Example 1 is shown schematically in FIG. 4. The cell 110 includes cell cover 116, retainer 118, platinum (Pt) anode 112, cathode 124 and a lithium ion conductive glass-ceramic (LiC-GC) 114 with lithium ion conductive barrier film 120 incorporated into a porous polyolefin flat-film membrane 122. The supported lithium ion conductive glass-ceramic-barrier film (LiC-GC-BF) multilayer is intercalated between cathode 124 and a lithium ion-rich electrolyte 18 (as shown in FIGS. 1 and 2). The cell further comprises supporting Teflon® sleeve structure 126 with gaskets 128. One gasket seals between the lithium ion conductive glass-ceramic (LiC-GC) and the housing to prevent leakage of the electrolyte from the anode compartment into the cathode compartment. The other gasket allows for even compression of the lithium ion conductive glass-ceramic (LiC-GC) by the Teflon® sleeve to prevent breakage of the lithium ion conductive glass-ceramic (LiC-GC) plate.

The cell 110 includes anode 112 that is a platinized titanium anode, 1"×4" rhodium and palladium jewelry plating. The cathode is a palladium cathode disc fabricated in-house, 1.4 inch round. The lithium ion conductive glass-ceramic (LiC-GC) 114 material is LICGC® G71-3 N33: DIA 2 IN×150 μm tape cast, 150 μm thick, 2 inch round from Ohara Corporation, 23141 Arroyo Vista, Rancho Santa Margarita, Calif. 92688.

The lithium ion conductive barrier film (Li—BF) 120 is fabricated from: a cyanoethyl polyvinyl alcohol (PVA-CN) polymer supplied by the Ulsan National Institute of Science and Technology in Ulsan South Korea, Dr. Hyun-Kon Song, procured from Alfa Aesar, stock number H61502; $LiPF_6$ (lithium hexafluorophosphate), 98%; EMC (ethyl methyl carbonate), 99%, from Sigma Aldrich, product number 754935; EC (ethylene carbonate), anhydrous, from Sigma Aldrich, product number 676802; and a porous membrane, ND420 polyolefin flat-film membrane from Asahi Corp.

The lithium ion conductive barrier film (Li—BF) 120 is fabricated in an argon purged glove bag. The glove bag is loaded with all materials, precision scale, syringes, and other cell components, then filled, and evacuated four times before the start of the electrolyte fabrication process.

The organogel electrolyte is mixed as follows: 4.0 ml of ethyl methyl carbonate (EMC) placed in a vial. Ethylene carbonate (EC) is liquefied by heating to about 140° F. and 2.0 ml of the ethylene carbonate (EC) is then added to the vial. 0.133 g (2% wt) cyanoethyl polyvinyl alcohol (PVA-CN) polymer is added to the vial and the mixture is agitated for 1 hour to dissolve the cyanoethyl polyvinyl alcohol (PVA-CN). Then 0.133 g (2% wt) fluoroethylene carbonate (FEC) is added as solid electrolyte interphase (SEI)-forming additive, and 0.972 g (1M) $LiPF_6$ is then added and mixed to complete the organogel electrolyte mixture. Alternatively, the electrolyte can be a 1.0 M $DMC-LiPF_6$ solution of 15.2 g $LiPF_6$ in 107.3 g dimethyl carbonate. The electrolytic cell is then assembled inside the glove bag. With the lithium ion conductive glass-ceramic (LiC-GC) and gaskets in place, the anode and cathode compartments are sealed from each other. The organogel electrolyte mixture is used to wet the cathode side of the lithium ion conductive glass-ceramic (LiC-GC), the Hipore™ membrane is placed on the cathode side of the lithium ion conductive glass-ceramic (LiC-GC) and wetted again with organogel electrolyte mixture. The cathode disc is then placed on top of the organogel mixture. The cell is placed in a Mylar® bag and sealed while still under argon purge. The sealed Mylar® bag with assembled cell is then placed in an oven at 60° C. for 24 hours to gel the electrolyte.

The electrolytic cell is removed from the oven and placed in the argon purged glove bag, and allowed to cool to room temperature. Clear polypro tape is used to seal the empty space above the cathode disc and secure the electrode wire. The electrolytic cell is now ready for use, is removed from the glove bag, and is connected to the electrolyte circulating system.

An electrolyte 18 is prepared with 120 g of lithium carbonate in 200 ml of deionized water and 500 ml of 20% wt sulfuric acid. The sulfuric acid is slowly added to the lithium carbonate suspension and mixed well. Undissolved lithium carbonate is allowed to settle. A supernatant is collected from the stock solution, an 18% wt lithium stock solution. The 18% wt lithium solution has a measured pH of 9. Solution pH is lowered by addition of 20% wt sulfuric acid. Again, the sulfuric acid is added slowly to minimize foaming. The 18% wt lithium stock solution is adjusted to pH 4.5. Preferred pH is between pH 3.0 and pH 4.5, most preferred is between pH 3.0 and pH 4.0, but the process can be run at a pH of 7.0 or below. A pH above 7.0 will result in carbonate in solution.

The electrolyte mixture is then poured into the circulating system. The circulating pump is primed and solution circulated for 30 minutes to check for leaks.

The lithium ion-rich electrolyte 18 flows through the top half of cell 110 over the lithium ion conductive glass-ceramic-barrier film (LiC-GC-BF) multilayer 114/120 and past anode 112. When potential is applied to the system, lithium metal builds up on the moving cathode below the lithium ion conductive glass-ceramic-barrier film (LiC-GC-BF) multilayer 114/120 system.

A Gamry Reference 3000 Potentiostat/Galvanostat/ZRA is attached to the cell 110. The pulse begins at 80 or 60 mAh for 2 seconds, then voltages at approximately 3 V to approximately 3.6 V. At voltages of 3-6 volts there is no significant activity. When the voltage is raised to 10V, the system responds. Amperage draw increases when the voltage is raised to 11 vdc. No gassing on the anode side of the cell was noted at 11 vdc. The Gamry Reference 3000 would not go above 11 vdc. Since no gassing occurred at 11 vdc, the reduction rate could most likely be much higher if voltage were increased. An even higher voltage and reduction rate are preferable if achieved with negligible oxygen production at the anode. The pH of the electrolyte at time zero is 4.46. The pH of the solution decreases to 4.29 after 35 minutes, and is 4.05 at the end of the experiment. The lowering pH indicates lithium ion removal from the electrolyte solution.

An amperage draw of 20 mA is noted at the start of the experiment. The amperage draw slowly increases to 60 mA after 30 minutes. Amperage holds fairly steady at this value for another 30 minutes. Experiment timer and graph are paused for 30 minutes to extend experiment (voltage held at 11 vdc). After approximately 65 minutes of run time, a large amperage spike and sudden vigorous gassing is noted on the anode side of the cell. This is indicative of lithium ion conductive glass-ceramic-barrier film (LiC-GC-BF) 114/120 membrane failure.

Rapid gassing and bright white flame is observed when the cell 110 is opened and cathode 124 is exposed to electrolyte leaking through the lithium ion conductive glass-ceramic-barrier film (LiC-GC-BF) 114/120, evidencing that the cell produces lithium metal by electrolysis of lithium ions in a sulfuric acid aqueous solution, through a lithium ion conductive glass-ceramic-barrier film (LiC-GC-BF) 114/120 membrane system.

Example 2

The cell used in Example 2 is shown schematically in FIG. 3D. The cell includes sleeve 1, cell body 3, cathode 5, anode 9, lithium ion conductive glass-ceramic (LiC-GC) membrane 2 with lithium ion conductive catholyte 10, lithium ion containing electrolyte 11, and O-ring 4 as a liquid seal between the two compartments. The supported lithium ion conductive glass-ceramic (LiC-GC) membrane 2 is intercalated between electrolyte 11 and catholyte 10. The cell further comprises supporting cathode 5 in contact with the catholyte 10 during deposition and anode 9 in the electrolyte 11. One O-ring 4 seals between the cell body and sleeve to prevent leakage of the electrolyte from the anode compartment into the cathode compartment.

The cell includes anode 9 that is compatible with strong sulfuric acid. A platinized titanium anode, 1"×4" rhodium and palladium jewelry plating was used in the test cell, however high over-potential anodes may not be required as there is no electrical path for electrolysis of water on the anode side of the cell. The cathode used was a palladium cathode disc fabricated in-house, 1.4 inch round; however this can be a different material compatible with the catholyte 10 and lithium metal. The lithium ion conductive glass-ceramic (LiC-GC) material is LICGC® G71-3 N33: DIA 2 IN×150 μm tape cast, 150 μm thick, 2 inch round from Ohara Corporation, 23141 Arroyo Vista, Rancho Santa Margarita, Calif. 92688.

Several electrolytes can be used for catholyte 10, including a simple lithium battery electrolyte such as lithium hexafluorophosphate solution in ethylene carbonate and dimethyl carbonate (EC-DMC-LiPF$_6$), a mixture of dimethyl carbonate and lithium hexafluorophosphate (DMC-LiPF$_6$), trifluoromethanesulfonyl-imide (TFSI) Ionic liquid based electrolytes such as N-butyl-N-methylpyrrolidinium bis(trifluoromethanesulfonyl)imide (Pyr$_{14}$TFSI), or ether based electrolytes such as, 1,3-dioxolane (ethylene glycol methylene ether), sulfone based electrolytes such as sulfones such as ethylmethylsulfone (EMS), methoxy-methylsulfone (MEMS) or tetramethylsulfone (TMS) are good candidates to produce lithium with solid electrolyte interphase (SEI) layers specifically for electric vehicle batteries that operate at high voltages, or a more complex lithium ion conducting barrier film (Li—BF).

The electrolyte 11 is prepared with 120 g of lithium carbonate in 200 ml of deionized water and 500 ml of 20% wt sulfuric acid. The sulfuric acid is slowly added to the lithium carbonate suspension and mixed well. Undissolved lithium carbonate is allowed to settle. A supernatant is collected from the stock solution, an 18% wt lithium stock solution. The 18% wt lithium solution has a measured pH of 9. Solution pH is lowered by addition of 20% wt sulfuric acid. Again, the sulfuric acid is added slowly to minimize foaming. The 18% wt lithium stock solution is adjusted to pH 4.5. Preferred pH is between pH 3.0 and pH 4.5, most preferred is between pH 3.0 and pH 4.0, but the process can be run at pH 7.0 or below. A pH above 7.0 will result in carbonate in solution.

The electrolyte mixture is then poured into the circulating system. The circulating pump is primed and solution circulated for 30 minutes to check for leaks.

The lithium ion-rich electrolyte 11 flows through the bottom half of cell body 3 over the lithium ion conductive glass-ceramic (LiC-GC) membrane 2 and past anode 9. When potential is applied to the system, lithium metal builds up on the cathode above the lithium ion conductive glass-ceramic (LiC-GC) membrane.

A Gamry Reference 3000 Potentiostat/Galvanostat/ZRA is attached to the cathode 5 and anode 9. The pulse begins at 80 or 60 mAh for 2 seconds, then volts at approximately 3 V to approximately 3.6 V. At voltages of 3-6 volts there is no significant activity. When the voltage is raised to 10V, the system responds. Amperage draw increases when voltage is raised to 11 vdc. No gassing on the anode side of the cell was noted at 11 vdc.

FIGS. 3A-3E illustrate an insertion/retraction module-adapted cell that includes a cathode support that positions the cathode. The support can be driven by a servo-motor or the like that transmits the cathode toward and away from forming lithium. A non-conductive sleeve 1 contains the liquid catholyte 10 and provides electrical insulation between the anode and cathode compartments.

To produce lithium, a lithium ion-containing acid electrolyte is directed through the anode side of the cell. The cathode side is filled with a suitable anhydrous electrolyte, then a cathode is inserted into the electrolyte, and potential is applied to initiate the electrolysis process. The cathode can be withdrawn, and formed lithium is harvested right off the cathode and the cathode reinserted.

This method provides a fully scalable and cost-effective automated production process. In one aspect, controls are built into the system to monitor current draw to each cell. A sudden increase in current draw indicates water electrolysis due to failure of a lithium ion conductive glass-ceramic (LiC-GC) membrane at which time the cathode can be retracted and that cell isolated from the acid electrolyte feed, other cells can continue production. The cell unit can then be changed out and production resumed on that cell.

Lithium carbonate is the process feed stock. Lithium carbonate having a purity as low as 90% may be used as the feed stock. The lithium carbonate is added to a sulfuric acid solution which releases $CO_2$ and places lithium ions into solution. Oxygen from the lithium carbonate reacts with the solution to neutralize hydronium ions or form hydroxyl ions (as noted by an increase in pH). Upon application of a potential across the electrolytic cell, lithium ions migrate through the lithium ion conductive glass-ceramic (LiC-GC) membrane and form lithium metal on the cathode, while oxygen is produced at the anode by conversion of hydroxyl ions or water back to hydronium ions (as noted by decrease in pH during electrolysis). According to the example, anode compartments and cathode compartments are decoupled electrically so that the only electron flow is that of lithium ions through the lithium ion conductive glass-ceramic (LiC-GC) membrane. Electrons are provided at the cathode convert lithium ions to lithium metal. Electrons are given up at the anode from water or hydroxyl ions (OH$^-$) that have been created during addition of lithium carbonate. Non-aqueous electrolyte on the cathode side of the cell can be any suitable liquid or gel electrolyte. For example, a lithium hexafluorophosphate solution in ethylene carbonate and dimethyl carbonate (EC-DMC-LiPF$_6$) mixture, or a lithium hexafluorophosphate solution in dimethyl carbonate (DMC-LiPF$_6$) mixture is suitable.

In the process of Example 2, a cathode is inserted into the cell at a spacing from the lithium ion conductive glass-ceramic (LiC-GC) membrane thereby dispensing with the barrier layer that is required by other processes. Cathode and anode compartments are not electrically coupled as proposed in other processes and instead are electrically isolated. Consequently, only lithium ion flows through the membrane. Electrolysis of water on the anode is prevented as is the associated parasitic electrical losses from water electrolysis. This permits the use of a higher voltage.

Electrolyte: $H_2SO_4 \rightarrow 2H^+ + SO_4^{2-}$ $H_2SO_4 \rightarrow H^+ + HSO_4^- \; HSO_4^- \rightarrow H^+ + SO_4^{2-}$ Feed stock reaction: $2Li_2CO_3 + 4H^+ + 4Li^+ + 2CO_2 + 2H_2O$ (reduces pH)

$2Li_2CO_3 + 2H^+ \rightarrow 4Li^+ + 2CO_2 + 2OH^-$ (reduces pH)

Anode reaction: $2H_2O \rightarrow 4H^+ + O_2 + 4e^-$ $2OH^- \rightarrow 2H^+ + O_2 + 2e^-$ Cathode reaction: $4Li^+(aq) + 4e^- \rightarrow 4Li(s)$ Net: $2Li_2CO_3 + \text{electricity} \rightarrow 4Li(s) + 2CO_2 + O_2$ $2Li_2CO_3 + \text{electricity} \rightarrow 4Li(s) + 2CO_2 + 2OH^-$ Example 3

Lithium metal was obtained using the cell and process conditions of Example 2, except that: stainless steel was used as anode, a copper disc was used as cathode, the cathode was stationary, and an insertion/retraction module was not implemented.

The lithium metal formed on the cathode 5 was analyzed using an inductively coupled plasma mass spectrometry (ICP-MS) method. Specifically, the high purity lithium metal is ionized with inductively coupled plasma and then subjected to mass spectrometry to separate and quantify the ions in the high purity lithium metal. The results are shown in Table 1 below:

TABLE 1

| | |
|---|---|
| Li | 99.9921 at %, including phosphorus |
| | 99.9648 wt %, including phosphorus |
| | 99.9997 wt % on metals basis (excluding phosphorus) |
| B | 0 |
| Na | 0 |
| Mg | 2.37 ppm |
| Al | 0 |
| P | 781 ppm |
| K | 0 |
| Ca | 0 |
| Cr | 0 |
| Mn | 0 |
| Fe | 1.8 ppm |
| Ni | 0 |
| Cu | Not tested |
| Zn | 1.1 ppm |
| Sr | Not tested |
| Ba | Not tested |

It is believed that the presence of phosphorus is due to the electrolyte $LiPF_6$ contained on the cathode side of the membrane. Notably, the extent of inclusion of phosphorous is limited to the film surface—the film-electrolyte interface. X-ray photoelectron spectroscopy (XPS) analysis confirmed the presence of phosphorous only on the film surface (up to 10 nm), with a more pure core of lithium metal below that depth. In an embodiment, post-processing steps can be included to remove phosphorus.

The lithium metal does not contain any ions other than lithium, magnesium, phosphorus, iron and zinc when analyzed by the inductively coupled plasma mass spectrometry (ICP-MS) method. Specifically, the lithium metal does not contain any of the following impurities: mercury, boron, sodium, aluminum, potassium, calcium, chromium, manganese, and nickel.

As shown in Table 1, the lithium metal has a lithium purity of at least 99.96 weight percent (including phosphorus), and at least 99.9997 weight percent on a metals basis (excluding phosphorus). However, the inventor believes that the presence of iron was due to the use of a stainless steel container to transport samples and that the iron impurity is therefore a result of lab handling and not the actual content of the lithium metal sample. Furthermore, the inventor believes that the presence of zinc and magnesium was due to errors resulting from the use of an air conditioner in the testing environment. Therefore, in an embodiment, the lithium metal may not contain any trace impurities. The inventor also believes that the presence of phosphorus is due to the use of a catholyte containing $LiPF_6$ which forms the resulting solid electrolyte interphase (SEI) layer. Therefore, in an embodiment, the lithium metal purity may be higher than 99.998 weight percent on a metals basis, and 100% using an electrolyte in catholyte 10 that does not form a solid electrolyte interphase (SEI) layer. These values can differ (can be controlled) because only lithium ions enter catholyte 10, and a variety of electrolytes can be used in catholyte 10, which result in the formation of an optimal solid electrolyte interphase (SEI) layer, or none at all.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A process of producing lithium hydroxide comprising:
   extracting lithium metal from a lithium salt using a selective lithium ion conducting layer that comprises an active metal ion conducting glass or glass-ceramic to provide a lithium metal product having a purity greater than 99.96 weight percent on a metals basis and comprising nanorod structures; and
   processing the lithium metal with deionized water to form lithium hydroxide and lithium hydroxide monohydrate that contain less than 0.3 ppm mercury.

2. An electrode comprising a cathode material produced from a feedstock that comprises lithium hydroxide monohydrate, wherein the lithium hydroxide monohydrate is obtained by a process as recited in claim 1.

3. A battery comprising an electrode produced from a feedstock that comprises lithium hydroxide, wherein the lithium hydroxide is obtained by a process as recited in claim 1.

4. A battery comprising an electrode produced from a feedstock that comprises lithium hydroxide monohydrate, wherein the lithium hydroxide monohydrate is obtained by a process as recited in claim 1.

5. A battery comprising an electrolyte containing lithium hydroxide, wherein the lithium hydroxide is obtained by a process as recited in claim 1.

* * * * *